United States Patent [19]
Rosenthal et al.

[11] Patent Number: 6,087,095
[45] Date of Patent: *Jul. 11, 2000

[54] DNA SEQUENCING METHOD

[75] Inventors: Andre Rosenthal; Sydney Brenner, both of Cambridge, United Kingdom

[73] Assignee: Medical Research Council, London, United Kingdom

[*] Notice: This patent is subject to a terminal disclaimer.

[21] Appl. No.: 08/325,224

[22] PCT Filed: Apr. 22, 1993

[86] PCT No.: PCT/GB93/00848

§ 371 Date: Dec. 9, 1994

§ 102(e) Date: Dec. 9, 1994

[87] PCT Pub. No.: WO93/21340

PCT Pub. Date: Oct. 28, 1993

[30] Foreign Application Priority Data

Apr. 22, 1992 [GB] United Kingdom ........... 9208733

[51] Int. Cl.[7] .............. C12Q 1/68; C12P 19/34; C07N 21/00
[52] U.S. Cl. .............. 435/6; 435/41; 435/172.1; 536/24.33; 536/25.3
[58] Field of Search ............. 435/6, 41, 172.1; 935/76, 77, 78; 536/23.1, 24.33, 25.3, 25.32

[56] References Cited

FOREIGN PATENT DOCUMENTS

WO 90/13666  11/1990  WIPO .
WO 91/06678  5/1991  WIPO .

OTHER PUBLICATIONS

Drmanac et al., "Sequencing of Megabase Plus DNA by Hybridization: . . . ", Genomics 4:114–128, 1989.

Salmeron et al., "Imaging of Biomolecules with the Scanning Tunneling Microscope: . . . ", J. Vac. Sci. Tech. 8:635, Jan./Feb. 1990.

Maxam et al., "A new method for sequencing DNA", Proc. Natl. Sci. USA 74:560–564, Feb. 1977.

Drmanac et al., "Reliable Hybridization of Oligonucleotides as Short as Six Nucleotides", DNA and Cell Biology 9:527, Nov. 1990.

Sanger et al., "DNA sequencing with chain–terminating inhibitors", Proc. Natl. Acad. Sci. USA 74:5463–5467, Dec. 1977.

Bains et al., "A Novel Method for Nucleic Acid Sequence Determination", J. Theor. Biol. 135:303–307, 1988.

Driscoll et al., "Atomic–scale imaging of DNA using scanning tunnelling microscopy", Nature 346:294, Jul. 1990.

E.D. Hyman, "A New Method of Sequencing DNA", Analytical Biochemistry 174:423–436, 1988.

Khrapko et al., "An oligonucleotide hybridization approach to DNA sequencing", FEBS 256:118–122, Oct. 1989.

P.A. Pevzner, "1–Tuple DNA Sequencing:Computer Analysis", J. Biom. Str. & Dyn. 7:63, 1989.

Jett et al., "Hig–Speed DNA Sequencing: An Approach Based Upon Fluorescence Detection . . . ", J. Biom. Str. & Dyn. 7:301, 1989.

Lindsay et al., Genet. Anal. Tech. Appl., 8:8, 1991.

Nguyen et al., Anal. Chem., 56:348, 1987.

Maskos et al., Cold Spring Harbor Symposium on Genome Mapping and Sequencing, Abstracts, p. 143, 1991.

Allison et al., Scanning Microsc. 4:517, 1990.

*Primary Examiner*—Nancy Degen
*Assistant Examiner*—Sean McGarry
*Attorney, Agent, or Firm*—Fulbright & Jaworski, LLP

[57] ABSTRACT

The invention is drawn to a method of DNA sequencing using labeled nucleotides that do not act as chain elongation inhibitors where the label is removed or neutralized for the sequential addition of non-labeled nucleotides.

16 Claims, 1 Drawing Sheet

DNA SEQUENCING METHOD

This application is a 371 of PCT/GB93/00848 filed Apr. 22, 1993.

The present invention relates to a method for sequencing DNA. In particular, the present invention concerns a method for the automated sequencing of large fragments of DNA.

DNA sequence analysis has become one of the most important tools available to the molecular biologist. Current sequencing technology allows sequence data to be obtained from virtually any DNA fragment. This has allowed not only the sequencing of entire genes and other genomic sequences but also the identification of the sequence of RNA transcripts, by the sequencing of cDNA. Currently, emphasis is being placed on genomic sequencing in order to determine the DNA sequence of entire genomes. Ultimately, it is hoped that the sequence of the human genome will be deciphered.

Traditional DNA sequencing techniques share three essential steps in their approaches to sequence determination. Firstly, a multiplicity of DNA fragments are generated from a DNA species which it is intended to sequence. These fragments are incomplete copies of the DNA species to be sequenced. The aim is to produce a ladder of DNA fragments, each a single base longer than the previous one. This can be achieved by selective chemical degradation of multiple copies of the DNA species to be sequenced, as in the Maxam and Gilbert method (A. Maxam and W. Gilbert, PNAS 74, p. 560, 1977). Alternatively, the DNA species can be used as a template for a DNA polymerase to produce a number of incomplete clones, as in the Sanger method (F. Sanger, S. Nicklen and A. Coulson, PNAS 74, p. 5463, 1977). These fragments, which differ in respective length by a single base, are then separated on an apparatus which is capable of resolving single-base differences in size. A thin polyacrylamide gel is invariably used in this process. The third and final step is the determination of the nature of the base at the end of each fragment. When ordered by the size of the fragments which they terminate, these bases represent the sequence of the original DNA species.

Determination of the nature of each base is achievers by previously selecting the terminal base of each fragment. In the Sanger method, for example, dideoxy nucleoside triphosphates (ddNTPs) are used to selectively terminate growing DNA clones at an A, C, G or T residue. This means that four separate reactions need to be performed for each sequencing exercise, each in a separate tube using a different ddNTP. In one tube, therefore, each labelled fragment will terminate with an A residue, while in the next tube with a C residue, and so on. Separation of each croup of fragments side-by-side on a polyacrylamide gel will show the sequence of the template by way of the relative size of the individual fragments.

In the Maxam and Gilbert method, on the other hand, the selectivity is achieved during the chemical degradation process. Chemicals are used which cleave DNA strands at A only, C only, G and A or T and C. Use of limiting concentrations of such chemicals allows partial digestion of the DNA species. As in the Sanger method, four separate reactions must be performed and the products separated side-by-side on a polyacrylamide gel.

The disadvantages of these prior art methods are numerous. They require a number of complex manipulations to be performed, in at least four tubes. They are susceptible to errors due to the formation of secondary structures in DNA, or other phenomena that prevent faithful replication of a DNA template in the Sanger method or which cause base-specificity to be lost by the chemical reactants of the Maxam and Gilbert method. The most serious problems, however, are caused by the requirement for the DNA fragments to be size-separated on a polyacrylamide gel. This process is time-consuming, uses large quantities of expensive chemicals, and severely limits the number of bases which can be sequenced in any single experiment, due to the limited resolution of the gel. Furthermore, reading the gels in order to extract the data is labour-intensive and slow.

A number of improvements have been effected to these sequencing methods in order to improve the efficiency and speed of DNA sequencing. Some of these improvements have related to the sequencing reaction itself. For example, improved polymerase enzymes have been introduced which lead to greater precision in the Sanger method, such as Sequenase® and Taquenase®. Improved reagents have not, however, significantly affected the speed of sequence data generation or significantly simplified the sequencing process.

In the interest of both speed and simplicity, a number of "Automated Sequencers" have been introduced in recent years (reviewed in T. Hunkapiller, R. Kaiser, B. Koop and L. Hood, Science, 254, p. 59, 1991). These machines are not, however, truly automatic sequencers. They are merely automatic gel readers, which require the standard sequencing reactions to be carried out before samples are loaded onto the gel. They do provide a slight increase in speed, however, due to faster reading of the gels and collation of the data generated into computers for subsequent analysis.

Many automated sequencers exploit recent developments which have been made in labelling technology. Traditionally, radioactive labels in the form of $^{32}$P or $^{35}$S have been used to label each DNA fragment. Recently, however, fluorophores have gained acceptance as labels. These dyes, attached either to the sequencing primer or to nucleotides, are excited to a fluorescent state on the polyacrylamide gel by a laser beam. An automated sequencer, therefore, can detect labelled fragments as they pass under a laser in a reading area. Use of dyes which fluoresce at different wavelengths allows individual labelling of A, G. C and T residues, which permits the products of all four sequencing reactions to be run in a single lane of the gel.

Even incorporating such refinements, however, automated sequencers can still produce no more than about 100 kb of finished sequence per person per year. At this rate, it would take one person 73,000 years to sequence the human genome.

Clearly, if the aim of sequencing the human genome is to be achieved, current sequencing technology is entirely inadequate. In view of this, a few proposals have been made for alternative sequencing strategies which are not merely improvements of the old technology.

One such method, sequencing by hybridisation (SBH), relies on the mathematical demonstration that the sequence of a relatively short (say, 100 kbp) fragment of DNA may be obtained by synthesising all possible N-mer oligonucleotides and determining which oligonucleotides hybridise to the fragment without a single mismatch (R. Drmanac, I. Labat, I. Bruckner and R. Crkvenjakov, Genomics, 4, p. 114, 1989; R. Drmanac, Z. Stvanovic, R. Crkvenjakov, DNA Cell Biology, 9, p. 527, 1990; W. Bains and G. Smith, J. Theor. Biol., 135, pp 303–307, 1988; K. R. Khrapko, et al, FEBS lett., 256, pp. 118–122, 1989; P. A. Pevzner, J. Biomolecular Structure and Dynamics, 7, pp. 63–73, 1989; U. Maskos and E. M. Southern, Cold Spring Harbour Symposium on Genome Mapping and Sequencing, Abstracts, p. 143, 1991). N can be 8, 9 or 10, such sizes being a compromise between the requirement for reasonable hybridisation parameters and manageable library sizes.

The technique can be automated by attaching the oligonucleotides in a known pattern on a two-dimensional grid. The fragment to be sequenced is subsequently hybridised to the oligonucleotides on the grid and the oligonucleotides to which the sequence has been hybridised are detected using a computerised detector. Determination of the sequence of the DNA is then a matter of computation. however, errors arise from the difficulty in determining the difference between perfect matches and single base-pair mismatches. Repetitive sequences, which occur quite commonly in the human genome, can also be a problem.

Another proposal involves the fluorescent detection of single molecules (J. Jett et al., J. Biomol. Struct. Dyn., 7, p. 301, 1989: D. Nguyen, et al., Anal. Chem., 56, p. 348, 1987). In this method, a single, large DNA molecule is suspended in a flow stream using light pressure from a pair of laser beams. Individual bases, each of which is labelled with a distinguishing fluorophore, are then cut from the end of the molecule and carried through a fluorescence detector by the flow stream.

Potentially, this method could allow the accurate sequencing of a large number of base pairs—several hundred—per second. However, feasibility of this method is not yet proven.

A third method is sequencing by scanning tunnelling microscopy (STM) (S. Lindsay, et al., Genet. Anal. Tech. Appl., 8, p. 8, 1991: D. Allison et al., Scanning Microsc., 4, p. 517, 1990: R. Driscoll et al., Nature, 346, p. 294, 1990: M. Salmeron et al., J. Vac. Sci. Technol., 8, p. 635, 1990). This technique requires direct three-dimensional imaging of a DNA molecule using STM. Although images of the individual bases can be obtained, interpretation of these images remains very difficult. The procedure is as yet unreliable and the success rate is low.

A fourth method involves the detection of the pyrophosphate group released as a result of the polymerisation reaction which occurs when a nucleotide is added to a DNA primer in a primer extension reaction (E. D. Hyman, Anal. Biochem., 174, p. 423, 1988). This method attempts to detect the addition of single nucleotides to a primer using the luciferase enzyme to produce a signal on the release of pyrophosphate. However, this method suffers a number of drawbacks, not least of which is that dATP is a substrate for luciferase and thus will always give a signal, whether it is incorporated into the chain or not. The added nucleotides are not labelled and no method is disclosed which will allow the use of labelled nucleotides.

In summary, therefore, each of the new approaches to DNA sequencing described above, while solving some of the problems associated with traditional methods, introduces several problems of its own. In general, most of these methods are expensive and not currently feasible.

There is therefore a need for a sequencing method which allows the rapid, unambiguous sequencing of DNA at low cost. The requirements for such a system are that:

1. it should not be based on gel resolution of differently-sized oligomers;
2. it should allow more rapid sequencing than present methods;
3. it should allow several DNA clones to be processed in parallel;
4. the cost of hardware should be reasonable;
5. it should cost less per base of sequence than current technology; and
6. it should be technically feasible at the present time

SUMMARY OF THE INVENTION

The present invention provides such a sequencing system which comprises a method for the sequential addition nucleotides to a primer on a DNA template.

According to a first aspect of the present invention, there is provided a method for determining the sequence of a nucleic acid comprising the steps of:

a) forming a single-stranded template comprising the nucleic acid to be sequenced;

b) hybridising a primer to the template to form a template/primer complex;

c) extending the primer by the addition of a single labelled nucleotide;

d) determining the type of the labelled nucleotide added onto the primer;

e) removing or neutralising the label; and f) repeating steps (c) to (e) sequentially and recording the order of incorporation of labelled nucleotides.

In the method of the invention, a single-stranded template is generated from a nucleic acid fragment which it is desired to sequence. Preferably, the nucleic acid is DNA. Part of the sequence of this fragment may be known, so that a specific primer may be constructed and hybridised to the template. Alternatively, a linker may be ligated to a fragment of unknown sequence in order to allow for hybridisation of a primer.

The template may be linear or circular. Preferably, the template is bound to a solid-phase support. For example, the template may be bound to a pin, a glass plate or a sequencing chip. The provision of a solid phase template allows for the quick and efficient addition and removal of reagents, particularly if the process of the invention is automated. Additionally, many samples may be processed in parallel in the same vessel yet kept separate.

Preferably, the template is attached to the solid support by means of a binding linker. For example, one of the commercially available universal primers can be ligated to the 5' end of the template or incorporated easily to one of the ends of the templates by the polymerase chain reaction.

The binding linker may be attached to the solid support by means of a biotin/streptavidin coupling system. For example, the surface of the solid support may be derivatised by applying biotin followed by streptavidin. A biotinylated binding linker is then ligated to the template to bind it to the solid support or the biotinylated template generated by PCR is bound to the solid support.

In an alternative embodiment, an unligated binding linker is bound to the solid support by the biotin/streptavidin system. The template is then hybridised to the binding linker. The binding linker may be a separate binding linker, which is not the sequencing primer. Alternatively, the binding linker may also function as the sequencing primer.

Clearly, it is essential in the latter embodiment that the template should possess a region of complementarity with the binding linker bound to the support. Where the template is ligated to a linker, the complementarity may be provided by that linker. Alternatively, the binding linker may be complementary to a unique sequence within the template itself.

Preferably the solid support is derivatised using a mask so as to allow high resolution packaging of the template(s) on the support. An array of template attachment areas can thereby be produced on a glass plate or sequencing chip, allowing parallel processing of a large number of different templates. Where pins are used as the solid support, a single pin is needed for each template. The single pins may be grouped into arrays. It is envisaged that an array of 100×100 pins or attachment areas can be used, to allow the simultaneous processing of $10^4$ clones.

The primer is extended by a DNA polymerase in the presence of a single labelled nucleotide, either A, C, G or T.

Suitable DNA polymerases are, for example, Sequenase 2.0®, T4 DNA polymerase or the Klenow fragment of DNA polymerase 1 as well as heat-stable polymerases such as Taq polymerase (for example Taquenase®) and Vent polymerase.

In a manually operated procedure using a single template, the labelled nucleotides are used singly and sequentially in order to attempt to add that nucleotide to the primer. The nucleotide will add on to the primer when it is complementary to the next nucleotide in the template. It may take one, two, three or four steps before the appropriate labelled nucleotide is used. However, as soon as it is determined that a labelled nucleotide has been added onto the primer, step (e) can be performed.

In an automated procedure, especially where a large number of templates are being sequenced simultaneously, in step (c) all four labelled nucleotides are used sequentially and it is merely noted which of the labelled nucleotides is added, that is it is determined whether it is the first, second, third or fourth labelled nucleotide which is added.

It has been found that nonspecific end-addition and misincorporation of nucleotides can lead to background problems when the incorporation step has been repeated a number of times. These side reactions are mainly due to the fact that a single nucleotide is present, instead of all four nucleoside triphosphates. In fact, it has been observed that while it is possible to sequence certain templates by the sequential addition of single nucleotides in the absence of the other three, significant problems have been encountered with other templates, particularly those templates containing multiple base repeats, due to non-specific incorporation of a nucleotide which is caused by the polymerase effectively jumping over a non-complementary base.

In order to ensure high accuracy of operation during the primer extension step, it has been found advantageous to carry out step (c) in the presence of chain elongation inhibitors.

Chain elongation inhibitors are nucleotide analogues which either are chain terminators which prevent further addition by the polymerase of nucleotides to the 3' end of the chain by becoming incorporated into the chain themselves, or compete for incorporation without actually becoming incorporated. Preferably, the chain elongation inhibitors are dideoxy nucleotides. Where the chain elongation inhibitors are incorporated into the growing polynucleotide chain, it is essential that they be removed after incorporation of the labelled nucleotide has been detected, in order to allow the sequencing reaction to proceed using different labelled nucleotides. It has been found, as described below, that 3' to 5' exonucleases such as, for example, exonuclease III, are able to remove dideoxynucleotides. This finding allows the use of dideoxynucleotides as chain elongation inhibitors to promote the accuracy of the polymerase in the sequencing method of the invention. Accuracy of the polymerase is essential if $10^4$ clones are to be processed simultaneously, since it is high polymerase accuracy which enables the sequencing reaction to be carried out on a single template instead of as four separate reactions.

Alternatively, the chain elongation inhibitors may be deoxynucleoside 5'-[α,β-methylene]triphosphates. These compounds are not incorporated into the chain. Other nucleotide derivatives such as, for example, deoxynucleoside diphosphates or deoxynucleoside monophosphates may be used which are also not incorporated into the chain.

It is furthermore envisaged that blocking groups on the 3' moiety of the deoxyribose group of the labelled nucleotide may be used to prevent nonspecific incorporation. Preferably, therefore, the labelled nucleotide is labelled by attachment of a fluorescent dye group to the 3' moiety of the deoxyribose group, and the label is removed by cleaving the fluorescent dye from the nucleotide to generate a 3' hydroxyl group. The fluorescent dye is preferably linked to the deoxyribose by a linker arm which is easily cleaved by chemical or enzymatic means.

Evidently, when nucleotide analogue chain elongation inhibitors are used, only the analogues which do not correspond to the labelled nucleotide should be added. Such analogues are referred to herein as heterogenous chain elongation inhibitors.

Label is ideally only incorporated into the template/primer complex if the labelled nucleotide added to the reaction is complementary to the nucleotide on the template adjacent the 3' end of the primer. The template is subsequently washed to remove any unincorporated label and the presence of any incorporated label determined. A radioactive label may be determined by counting or any other method known in the art, while fluorescent labels can be induced to fluoresce, for example by laser excitation.

It will be apparent that any label known in the art to be suitable for labelling nucleic acids may be used in the present invention. However, the use of fluorescent labels is currently preferred, due to the sensitivity of detection systems presently available for such labels which do not involve the use of radioactive substances.

Examples of flourescently-labelled nucleotides currently available include fluorescein-12-dUTP, fluorescein-15-dCTP, fluorescein-15-dATP and flurescein-15-dITP. It has proved very difficult to synthesise a suitable fluroescent guanosine compound, so an inosine compound is used in its place. Should a fluorescent guanosine compound become available, its use is envisaged in the present invention.

It has been found advantageous to use a mixture, of unlabelled and labelled nucleotides in the addition step.

When a fluorescent label is used, in order to produce all possible extension products on a template possessing a run of a particular nucleotide, the following ratios were found to be approximately optimal:

Fluorescein—15-dATP/dATP 500:1
Fluorescein—15-dITP/dGTP 500:1
Fluorescein—12-dUTP/dTTP 15:1
Fluorescein—12-dCTP/dCTP 15:1.

Preferably, therefore, the above ratios are used in connection with fluorescently-labelled nucleotides.

By repeating the incorporation and label detection steps until incorporation is detected, the nucleotide on the template adjacent the 3' end of the primer may be identified. Once this has been achieved, the label must be removed before repeating the process to discover the identity of the next nucleotide. Removal of the label may be effected by removal of the labelled nucleotide using a 3'–5' exonuclease and subsequent replacement with an unlabelled nucleotide. Alternatively, the labelling group can be removed from the nucleotide. In a further alternative, where the label is a fluorescent label, it is possible to neutralise the label by bleaching it with laser radiation.

If chain terminators or 3' blocking groups have been used, these should be removed before the next cycle can take place. Preferably, chain terminators are removed with a 3'–5' exonuclease. Preferably, exonuclease III is used. 3' blocking groups may be removed by chemical or enzymatic cleavage of the blocking group from the nucleotide.

Where exonuclease III is used to remove the chain terminators, it is essential to prevent the exonuclease III from chewing back along the growing chain to remove nucleotides which have already been incorporated, or even the primer itself. Preferably, therefore, a nucleoside derivative which is resistant to removal by exonucleases is used to replace the labelled nucleotides. Advantageously deoxynucleoside phosphorothioate triphosphates ($d_sNTPs$) are used. Likewise, the primer preferably comprises a phosphorothioate nucleoside base(s) at its 3' end which are incorporated during primer synthesis or an extra enzymatic capping step.

It is known that deoxynucleoside phosphorothioate derivatives resist digestion by exonuclease III (S. Labeit et al., DNA, 5, p. 173, 1986). This resistance is, however, not complete and conditions should be adjusted to ensure that excess digestion and removal of phosphorothioate bases does not occur.

For example, it has been found that the pH of the exoIII buffer used (50 mM Tris/HCl, 5 mM $MgCl_2$) affects the extent of chewing back which occurs. Experiments carried out at pH 6.0, 7.0, 7.5, 8.0, 8.5, 9.0 and 10.0 (37° C.) reveal that pH 10.0 is the optimum with respect to the rate of reaction an specificity of exoIII. At this pH, the reaction wets show to go to completion in less than 1 minute with no detectable chewing back.

Once the label and terminators/blocking groups have been removed, the cycle is repeated to discover the identity of the next nucleotide.

In an alternative embodiment of the invention, steps (c) and (d) of the first aspect of the invention are repeated sequentially a plurality of times before removal or neutralisation of the label.

The number of times the steps (c) and (d) can be repeated depends on the sensitivity of the apparatus used to detect when a labelled nucleotide has been added onto the primer. For instance, if each nucleotide is labelled with a different fluorescent label, the detection apparatus will need to be able to distinguish between each of the labels and will ideally be able to count the number of each type of fluorescent label. Alternatively, where each nucleotide is radioactively labelled or labelled with the same fluorescent dye, the apparatus will need to be able to count the total number of labels added to the primer.

As with the first embodiment of the invention, in a manual procedure using a single template, the labelled nucleotides are used singly and sequentially until a labelled nucleotide is added, whereupon the sequence is repeated. In an automated procedure all four labelled nucleotides are used sequentially and the apparatus is programmed to detect which nucleotides are added in what sequence to the primer.

Once the number of labels added has reached the resolving power of the detecting apparatus, removal or neutralisation of the label is carried out in a single step. Thus, the number of label removal steps is significantly reduced.

In this alternative embodiment, the steps (c) and (d) of the first aspect of the invention will preferably comprise:
  i) adding a labelled nucleotide together with three heterogenous chain elongation inhibitors which are not incorporated into the chain, such as 5'-[α,β-methylene] triphosphates;
  ii) removing excess reagents by washing;
  iii) determining whether the label has been incorporated; and
  iv) repeating steps (i) to (iii) using a different labelled nucleotide, either until a labelled nucleotide has been incorporated or until all four labelled nucleotides have been used.

This technique necessitates the use of a more sophisticated counter or label measuring device. Allowing for runs of repeated nucleotides, the label measuring device should be able to detect the presence of between four and sixteen labelled nucleotides accurately. For the measurement of long stretches of repeated nucleotides, a device with a greater capacity may be required.

Scheme 1

According to a preferred aspect of the invention, a DNA fragment is sequenced according to the following scheme:
  1) a capped primer containing a phosphorothioate nucleoside derivative is hybridized to a template to form a template/primer complex;
  2) a labelled deoxynucleoside triphosphate (dNTP) together with heterogenous chain terminators and a suitable polymerase is added to the template/primer complex;
  3) excess reagents are removed by washing;
  4) the amount of incorporated label is measured;
  5) the template/primer complex is treated with a exonuclease to remove the label and the dideoxynucleotides;
  6) the exonuclease is removed by washing;
  7) a phosphorothioate deoxynucleoside triphosphate corresponding to the labelled deoxynucleoside triphosphate added in Step 2 is added together with heterogenous chain terminators;
  8) excess reagents are removed by washing;
  9) the template/primer complex is treated with an exonuclease to remove the chain terminators;
  10) the exonuclease is removed by washing; and
  11) repeating step 2) to 10) four times, each time with a different labelled nucleotide, together with the appropriate heterogenous chain terminators.

For example, in Step 2 above the labelled nucleotide could be dATP. In this case, the heterogeneous chain terminators could be ddGTP, ddTTP and ddCTP. In step 7 phosphorothioate dATP would be added to replace the labelled dATP removed with the exonuclease in step 6. The cycle can then be repeated with another labelled nucleotide, for example dGTP, together with the heterogeneous dideoxynucleotides ddATP, ddTTP and ddCTP. This will cause label to be incorporate in all the chains propagating with G. This is followed in turn with labelled dTTP and labelled dCTP and continued again with dATP, dGTP, dTTP and dCTP and so on.

Scheme 2

According to a second preferred aspect of the invention, a DNA fragment is sequenced according to the following scheme:
  1) a capped primer containing a phosphorothioate nucleoside derivative is hybridized to a template to form a template/primer complex;
  2) a labelled deoxynucleotide together with heterogeneous chain terminators and a suitable polymerase is added to the template/primer complex;
  3) excess reagents are removed by washing;
  4) the amount of incorporated label is measured;
  5) the labelled nucleotide and the chain terminators are removed with an exonuclease;
  6) the exonuclease is removed by washing;
  7) a phosphorothioate deoxynucleotide together with heterogeneous chain elongation inhibitors not incorporated into the chain is added;
  8) excess reagents are removed by washing; and
  9) steps 2) to 8) are repeated four times, each time with a different labelled nucleotide.

This scheme is essentially a sub-scheme of scheme 1. The main difference is that during the capping step 7, dideoxynucleotides are replaced by the corresponding 5'-[α,β-methylene]triphosphates derivatives. However, other chain elongation inhibitors like deoxynucloside diphosphate or deoxynucleoside monophosphate derivatives may also be used. Since these derivatives cannot be incorporated into the growing polynucleotide chain there is no need to remove them. Hence, scheme 2 completely lacks the last exonuclease treatment step and the subsequent washing step of scheme 1.

Scheme 3

According to a third preferred aspect of the invention, a DNA fragment is sequenced according to the following scheme:

1) a capped primer containing a phosphorothioate deoxynucleotide is hybridised to a template to form a template/primer complex;
2) a labelled nucleotide triphosphate together with heterogeneous chain elongation inhibitors not incorporated into the chain is added;
3) excess reagents are removed by washing;
4) the amount of incorporated label is measured;
5) steps 2 to 4, adding different labelled nucleotides in the presence of their corresponding heterogeneous chain elongation inhibitors not incorporated into the chain, are repeated until all four labelled nucleotides have been added;
6) all labelled nucleotides are removed with exonuclease;
7) the exonuclease is removed by washing;
8) the phosphorothioate deoxynucleotide corresponding to the first labelled deoxynucleotide added to the reaction in step 2, is added together with heterogenous claim elongation inhibitors not incorporated into the chain and a suitable polymerase;
9) excess reagents are removed by washing; and
10) steps 8 and 9 are repeated with the three remaining phosphorothioate deoxynucleoside derivatives.

This scheme has the notable advantage of reducing overall number of exonuclease steps. All four labelled nucleotides are sequentially added to the chain and individually detected before all incorporated nucleotides are removed by a single exonuclease digestion step. The chase reactions are then carried out sequentially with the appropriate phosphorothioate nucleoside derivatives.

Scheme 4

In a fourth preferred aspect of the invention, a DNA fragment is sequenced according to the following scheme:

1) a capped primer is hybridized to a template to form a template/primer complex;
2) a fluorescent nucleoside triphosphate, together with three heterogeneous chain elongation inhibitors not incorporated into the chain and a suitable polymerase, is added;
3) excess reagents are removed by washing;
4) the amount of incorporated label is measured;
5) steps 2 to 4 are repeated using all three different nucleoside triphosphates, each with a fluorescent label, in the presence of the respective heterogeneous chain elongation inhibitors not incorporated into the chain.
6) the fluorescent labels are destroyed by bleaching with a laser or by a suitable chemical reaction, or the fluorescent labels are removed by a chemical cleavage step.

This scheme has the advantage that no enzymatic removal of incorporated label by way of an exonuclease reaction is required, nor is a chasing reaction with a phosphorothioate nucleotide derivative necessary. Instead, all incorporated fluorophores are chemically destroyed using either laser bleaching technology or suitable chemical reactions to destroy the dye or cleave the dye from the nucleotides.

Preferably, if the detector used permits quantitative measurement of incorporated label, the bleaching or cleaving step need only be carried out from time to time rather than after each successive addition.

Scheme 5

According to a fifth preferred aspect of the invention a DNA fragment is sequenced according to the following scheme:

1) a capped primer is hybridized to a template;
2) a nucleoside triphosphate labelled by attachment of a fluorescent dye group via a linker arm to the 3' moiety of the deoxyribose sugar thereon is added;
3) excess reagents are removed by washing;
4) the amount of incorporated label is measured;
5) the fluorescent dye group is removed by enzymatic cleavage; and
6) excess reagents are removed by washing.

In Scheme 5, the nonspecific addition of labelled nucleotide is prevented by the 3' modification, so that the labelled nucleotide effectively acts as a chain terminator. Removal of the 3' blocking group is then all that is required to allow chain elongation to continue.

In a further aspect of the invention, there is provided sequencing kit comprising at least three of the following:

i) a linker for attaching a DNA template to a solid-phase matrix, the linker comprising a primer having a deoxynucleoside phosphorothioate residue at its 3' end;
ii) chain elongation inhibitors;
iii) fluorescently-labelled nucleoside triphosphates;
iv) deoxynucleoside phosphorothioate triphosphates;
v) a 5'→3' DNA polymerase;
vi) a 3'→5' exonuclease.

In addition, such a kit may comprise a solid support for carrying out the reaction, as well as biotinylated primers or linkers and biotin/streptavidin reagents for coupling the linker to the solid support. The 3'–5' exonuclease may be exonuclease III. Furthermore, alternative chain elongation inhibitors, such as 3'-deoxyribose blocked labelled nucleotides, may be included. Preferably, the kit will comprise all of the components i–vi.

The invention also comprises an automatic sequencing machine capable of sequencing a nucleic acid essentially by executing the steps of a method according to the invention.

The machine is adapted either to move the solid support carrying the template(s) into and out of all the necessary reagent and washing solutions, or to pump reagents and washing solutions over the solid support sequentially. The pin array type of support is better suited to the first procedure, while glass plates and sequencing chips are more appropriate to the second.

Several washing steps are included between each reagent addition to minimise the carry-over of reagents.

The presence of label may be determined, in the case of a chip array, by passing the array over a fixed detector which records the level of label relative to the position of the array over the detector. In the case of a fixed glass plate or sequencing chip array, a radioactive or fluorescent image may be obtained by a fixed detector positioned above the array. Alternatively, the glass plate or sequencing chip array and/or the detector may be movable. A two-dimensional image is produced by the detector and analysed by a computer.

Alternatively, optical fibres connected directly to a sequencing chip or to the pins in a pin array may be used to transmit data to a processor if used together with fluorescent labels.

DRAWINGS

The invention will now be described, for the purpose of illustration only, with reference to the following figures:

FIG. 1 is a graph showing the correlation of emitted fluorescence to the number of nucleotides incorporated, using dUTP-12-fluorescein; and FIG. 2 is as FIG. 1 except that dCTP-12-fluorescin is used.

DESCRIPTION OF PREFERRED EMBODIMENTS

EXAMPLES

Example 1

Figure 1:
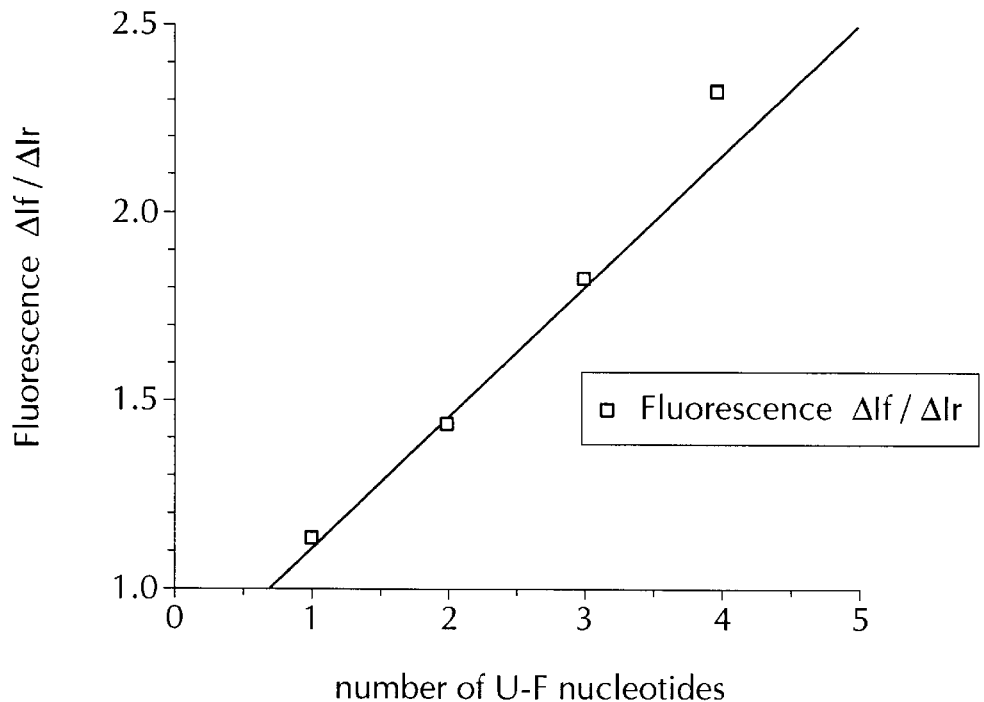

Preparation of the DNA Template/Primer Complex 1

Generation of Template and Binding to Solid Support

In this example an anchored single-stranded PCR product was used which was generated by known methods (T. Hultman et al., Nucleic Acids Res., 17, (1989), 4937–4946; D. S. C. Jones et al., DNA Sequence, 1 (1991), 279–283). Briefly, the template was generated by the polymerase chain reaction (PCR) using one biotinylated primer and one normal primer and the product subsequently bound to streptavidin coated magnetic beads. By treating the anchored double-stranded PCR product with alkali the non-anchored template strand is removed. All the steps were carried out as follows: PCR was performed in 50 µl using 0.5 ml test tubes. The following items were added: 30 µl water, 5 µl of 10× PCR buffer (Cetus), 5 µl of 2.5 mM dNTP's, 2.5 µl of 10 µM of the 5'-biotinylated universal reverse primer with the sequence: 5' Bio-AACAGCTATGACCATG 3', 2.5 µl of 10 µM of the (−20) universal forward primer with the sequence: 5' GTAAAACGACGGCCAGT 3', 1 µl of the Bluescript KS plasmid DNA at the concentration 1 ng/µl, 0.5 µl (2.5 units) of native Taq polymerase (Cetus). After overlaying with light mineral oil the following cycles were performed: 95° C. 90s, [95° C. 30s, 55° C. 60s, 72° C. 60s]×35, 72° C. 180s. All cycles were performed using the maximum heating and cooling rates possible with the Techne PHC-1 or PHC-2.

Binding the biotinylated PCR product with a length of approximately 250 bp to the streptavidin-coated magnetic beads (Dynal) is accomplished by incubating 100 µl of beads under mineral oil at room temperature for 5 min. The beads are sedimented using a strong magnet and the supernatant including the mineral oil is removed. Further traces of unused nucleotides, primers and buffers are removed by washing the beads with 100 µl of water. The nonbiotinylated DNA strand is removed by incubating the beads with 50 µl of 0.15M NaOH for 5 min. at room temperature. The beads are sedimented and the supernatant is removed, followed by a further treatment with 50 µl of 0.15M NaOH and three washings with 100 µl of water. Finally the beads were resuspended in 10 µl of water.

Annealing of the Sequencing Primer to the Anchored Single-Stranded DNA Template

To the 10 µl resuspended beads with the anchored single-stranded DNA template (approximately 2 pmoles), 4 µl of 5× Sequenase annealing buffer (200 mM Tris/HCl pH 7.5 100 mM MgCl$_2$, 250 mM NaCl, USB), and 4 µl (4 pmoles) of T7 primer with the sequence: 5' AATACGACTCAC-TATAG 3' are added. The mixture is heated for 3 min. at 65° C. and then cooled on ice. The template/primer complex is now ready for sequencing. The following figure displays parts of its structure:

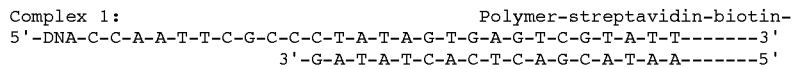

```
Complex 1:                                              Polymer-streptavidin-biotin-
         5'-DNA-C-C-A-A-T-T-C-G-C-C-C-T-A-T-A-G-T-G-A-G-T-C-G-T-A-T-T-------3'
                                   3'-G-A-T-A-T-C-A-C-T-C-A-G-C-A-T-A-A-------5'
```

Capping of the Primer with Thionucleotides

To the 18 µl annealing mixture add 10 µl of 100 µM d$_s$GTP, d$_s$CTP, ddATP, ddTTP, and 4 µl (5 units) of diluted sequenase 2.0 (USB), and incubate the mixture for 2 min. at room temperature. According to the complementary strand, this adds the following five nucleotides sequentially to the primer: d$_s$G, d$_s$G, d$_s$C, d$_s$G, and ddA. The beads were sedimented using the magnet and the supernatant removed. The beads were then washed two times with 50 µl water.

Removing the Dideoxynucleotide from the Capped Primer

To the bead 10 µl (20 units) of an exonuclease solution in 50 mM Tris/HCl pH 7.5, 5 µM MgCl$_2$, 5 mM DTT were added and the mixture incubated 2 min. at 37° C. The reaction was stopped by sedimenting the beads with the magnet and removing the supernatant, followed by three washings with 50 µl of water. This step removed the dideoxy A-nucleotide from the 3'-end of the primer.

Sequencing by Sequential Addition of Single Labelled Nucleotides: First Complete Cycle of 9 Steps Scheme 1

Steps 2 and 3

The beads (anchored template/primer complex 1) where resuspended in 13 µl water. The following items were added: 5 µl 5× sequenase buffer, 10 µl of a nucleotide mixture containing 10 µCi of alpha-$^{32}$P dATP of specific activity of 400 Ci/mmole, 4µM cold dATP, 100 µM ddGTP, 100 µM ddTTP, 100 µM ddCTP, and 4 µl of diluted sequenase 2.0. The mixture was incubated for 2 min at 37° C. and the reaction stopped by sedimenting the beads with the magnet and removing the supernatant followed by three further washings with 5 µl of water. In this step, according to the complementary strand, two A-nucleotides and one dideoxy T-nucleotide were added to the 3'-end of the capped primer.

Step 4

The label is counted with a hand counter.

Steps 5 and 6

The dideoxynucleotide and the labelled nucleotides were removed by adding 10 µl (20 units) of an exonuclease III solution in 50 mM Tris/HCl pH 7.5, 5 mM MgCl$_2$, 5 mM DTT and incubating the mixture for 2 min. at 37° C. The reaction was stopped by sedimenting the beads with the magnet and removing the supernatant, followed by three washings with 50 µl of water. The removal of the label was checked by measuring the mixture with the hand counter.

Steps 7 and 8

In order to cap the primer, the beads were resuspended in 13 µl water. The following items were added: 5 µl 5× sequenase buffer, 10 µl of a nucleotide mixture containing 100 µM d$_s$ATP, 100 µM ddGTP, 100 µM ddTTP, 100 µN ddCTP, and 4 µl of diluted sequenase 2.0. The mixture was incubated 2 min. at 37° C. and the reaction stopped by sedimenting the beads with the magnet and removing the supernatant followed by three further washings with 50 µl of water. In this step, two thiolated A-nucleotides and one dideoxy T-nucleotide were added to the sequencing primer.

Steps 9 and 10

The dideoxy nucleotide was removed by adding 10 µl (20 units) of the above specified exonuclease III solution and incubating the mixture for 2 min. at 37° C. The reaction was stopped by sedimenting the beads with the magnet and removing the supernatant, followed by three washings with 50 µl of water.

Sequencing by Sequential Addition of Single Nucleotides: Second Complete Cycle of 9 Steps Scheme 1

Steps 2 and 3

The beads (anchored template/primer complex 1) were resuspended in 13 µl water. The following items were added: 5 µl of 5× sequenase buffer, 10 µl of a nucleotide mixture containing 10 µCi of alpha-$^{32}$P dTTP of specific activity of 400 Ci/mmol, 4 µM cold dTTP, 100 µM ddGTP, 100 µM ddATP, 100 µM ddCTP, and 4 µl of diluted sequenase 2.0. The mixture was incubated 2 min. at 37° C. and the reaction stopped by sedimenting the beads with the magnet and removing the supernatant followed by three further washings with 50 µl of water. In this step, according to the complementary strand, two T-nucleotides and one dideoxy G-nucleotide were added to the 3'-end of the capped primer.

Step 4

The label is counted with a hand counter.

Steps 5 and 6

The dideoxynucleotide and the labelled nucleotides were removed by adding 10 µl (20 units) of the above specified exonuclease III solution and incubating the mixture for 2 min at 37° C. The reaction was stopped by sedimenting the beads with the magnet and removing the supernatant, followed by three washings with 50 µl of water. The removal of the label was checked by measuring the mixture with the hand counter.

Steps 7 and 8

In order to cap the primer, the beads were resuspended in 13 µl water. The following items were added: 5 µl of 5× sequenase buffer, 10 µl of a nucleotide mixture containing 100 µM d$_s$TTP, 100 µM ddGTP, 100 µM ddATP, 100 µM ddCTP, and 4 µl of diluted sequenase 2.0. The mixture was incubated 2 min. at 37° C. and the reaction stopped by sedimenting the beads with the magnet and removing the supernatant followed by three further washings with 50 µl of water. In this step, two thiolated T-nucleotides and one dideoxy G-nucleotide were added to the sequencing primer.

Steps 9 and 10

The dideoxy nucleotide was removed by adding 10 µl (20 units) of the above specified exonuclease III solution and incubating the mixture for 2 min. at 37° C. The reaction was stopped by sedimenting the beads with the magnet and removing the supernatant, followed by three washings with 50 µl of water.

Example 2

This experiment was carried out in order to confirm that all the reactions described in example 1 yielded the correct elongation as well as degradation products. To prove this, the experiment described in example 1 was repeated using a $^{32}$P-labelled primer in combination with cold nucleotides. The following modifications were made:

1. 4 pmoles of a 5'-$^{32}$P-labelled sequencing primer with the sequence 5' AATACGACTCACTATAG 3' was used in the annealing step;
2. In step 2 of the first cycle the labelled compound α-$^{32}$P-dATP was omitted from the nucleotide mixture and the concentration of the cold dATP was increased to 100 µM;
3. In step 2 of the second cycle the labelled compound α-$^{32}$-dTTP was omitted from the nucleotide mixture and the concentration of the cold dTTP was increased to 100 µM;
4. Step 4 in both cycles was not necessary;
5. After each enzymatic reaction and subsequent washing a $^{1}\!/_{100}$ aliquot of the beads were removed and placed in separate 0.5 ml test tube.

After performing all steps described in example 1, 5 µl of 90% formamide dye mix were added to all the individual bead aliquots, the mixtures heated for 3 min. at 95° C., centrifuged at 13,000 g for 5 seconds and cooled on ice. A small aliquot (1 µl) of each sample was loaded into a individual well of a 20% polyacrylamide gel containing 7M urea and electrophoresed at 700 Volts for 3 to 4 hours. After electrophoresis the upper glass plate was removed and the exposed to a X-ray film for approximately 2 to 4 hrs. The band pattern obtained was in full agreement with the predicted length of all primer elongation and degradation products.

Example 3

Preparation of Anchored DNA Template/Primer Complex 2

Annealing and Binding of the Template/Primer Complex to Solid Support

In this example the biotinylated sequencing primer was first annealed to the complementary region of a single-stranded M13 template and the complex subsequently bound via the 5' biotin moiety of the primer to the solid support (streptavidin beads). 2 µg (1 pmole) of M13mp18 DNA was combined with 2 pmoles of 5' biotinylated (−20) universal forward primer with the sequence 5' GTAAAACGACGGC-CAGT 3' in 40 mM Tris/HCl pH 7.5, 20 mM MgCl$_2$, 50 mM NaCl in a total of 10 µl. The mixture was heated for 3 min. at 65° C. and slowly cooled down to room temperature over a period of 10 min. 30 µl of streptavidin-coated magnetic beads (Dynal) were added and the mixture incubated for 5 minutes at room temperature. The beads were sedimented, the supernatant removed, and the beads resuspended in 10 µl of water.

Capping of the Primer with Thionucleotides

To the 18 µl annealing mixture add 10 µl of 100 µM d$_s$GTP ddATP, ddTTP, ddCTP, and 4 µl (5 units) of diluted sequenase 2.0 (USB), and incubate the mixture for 2 min. at room temperature. According to the complementary strand this adds the following two nucleotides sequentially to the primer: $d_sG$ and ddA. The beads were sedimented using the magnet and the supernatant removed. The beads were then washed two times with 50 µl water.

Removing the Dideoxynucleotide from the Capped Primer

To the bead 10 µl (20 units) of an exonuclease solution in 50 mM Tris-Hcl pH 7.5, 5 mM MgCl2, 5 mM DTT were added and the mixture incubated 2 min. at 37° C. The reaction was stopped by sedimenting the beads with the magnet and removing the supernatant, followed by three washings with 50 µl of water. This step removed the dideoxy A-nucleotide from the 3'-end of the primer.

Sequencing by Sequential Addition of Single Labelled Nucleotides: First Complete Cycle of 9 Steps Scheme 1

Steps 2 and 3

The beads (anchored template/primer complex 1) were resuspended in 13 µl water. The following items were added: 5 µl 5× sequenase buffer, 10 µl of a nucleotide mixture containing 10 µCi of alpha-$^{32}$P dATP of specific activity of 400 Ci-mmol, 4 µM cold dATP, 100 µM ddGTP, 100 µM ddTTP, 100 µM ddCTP, and 4 µl of diluted sequenase 2.0. The mixture was incubated for 2 min at 37° C. and the reaction stopped by sedimenting the beads with the magnet and removing the supernatant followed by three further washings with 50 µl of water. In this step, according to the complementary strand, two A-nucleotides and one dideoxy T-nucleotide were added to the 3' end of the capped primer.

Step 4

The label is counted with a hand counter.

Steps 5 and 6

The dideoxynucleotide and the labelled nucleotides were removed by adding 10 µl (20 units) of an exonuclease III solution in 50 mM Tris/HCl pH 7.5 mM $MgCl_2$, 5 µM DTT and incubating the mixture for 2 min. at 37° C. The reaction was stopped by sedimenting the beads with the magnet and removing the supernatant, followed by three washings with 50 µl of water. The removal of the label was checked by measuring the mixture with the hand counter.

Steps 7 and 8

In order to cap the primer, the beads were resuspended in 13 µl water. The following items were added: 5 µl 5× sequence buffer, 10 µl of a nucleotide mixture containing 100 µM $d_sATP$, 100 µM ddGTP, 100 µM ddTTP, 100 µM ddCTP, and 4 µl of diluted sequenase 2.0. The mixture was incubated 2 min. at 37° C. and the reaction stopped by sedimenting the beads with the magnet and removing the supernatant followed by three further washings with 50 µl of water. In this step, two thiolated A-nucleotides and one dideoxy T-nucleotide were added to the sequencing primer.

Steps 9 and 10

The dideoxy nucleotide was removed by adding 10 µl (20 units) of the above specified exonuclease III solution and incubating the mixture for 2 min. at 37° C. The reaction was stopped by sedimenting the beads with the magnet and removing the supernatant, followed by three washings with 50 µl of water.

Sequencing by Sequential Addition of Single Nucleotides: Second Complete Cycle of 9 Steps Scheme 1

Steps 2 and 3

The beads (anchored template/primer complex 1) were resuspended in 13 µl water. The following items were added: 5 µl of 5× sequenase buffer, 10 µl of a nucleotide mixture containing 10 µCi of alpha-$^{32}$-P dTTP of specific activity of 400 Ci/mmol, 4 µM cold dTTP, 100 µM ddGTP, 100 µM ddATP, 100 µM ddCTP, and 4 µl of diluted sequenase 2.0. The mixture was incubated 2 min. at 37° C. and the reaction stopped by sedimenting the beads with the magnet and removing the supernatant followed by three further washings with 50 µl of water. In this step, according to the complementary strand, two T-nucleotides and one dideoxy C-nucleotide were added to the 3-end of the capped primer.

Step 4

The label is counted with a hand counter.

Steps 5 and 6

The dideoxynucleotide and the labelled nucleotides were removed by adding 10 µl (20 units) of the above specified exonuclease III solution and incubating the mixture for 2 min. at 37° C. The reaction was stopped by sedimenting the beads with the magnet and removing the supernatant, followed by three washings with 50 µl of water. The removal of the label was checked by measuring the mixture with the hand counter.

Steps 7 and 8

In order to cap the primer, the beads were resuspended in 13 µl water. The following items were added: 5 µl of 5× sequenase buffer, 10 µl of a nucleotide mixture containing 100 µM $d_sTTP$, 100 µM ddGTP, 100 µM ddATP, 100 µM ddCTP, and 4 µl of diluted sequenase 2.0. The mixture was incubated 2 min. at 37° C. and the reaction stopped by sedimenting the beads with the magnet and removing the supernatant followed by three further washings with 50 µl of water. In this step, two thiolated T-nucleotides and one dideoxy C-nucleotide were added to the sequencing primer.

Steps 9 and 10

The dideoxy nucleotide was removed by adding 10 µl (20 units) of the above specified exonuclease III solution and incubating the mixture for 2 min. at 37° C. The reaction was stopped by sedimenting the beads with the magnet and removing the supernatant, followed by three washings with 50 µl of water.

Example 4

Preparation of the DNA Template/Primer Complex 2

Template preparation, binding of the template to solid support, and annealing of the sequencing primer was performed as described in example 1, except that in the annealing step 4 µl (4 pmoles) of radio-labelled T7 primer with the sequence: $^{32}$P-5'AATACGACTCACTATAG 3' are used.

Template/primer Complex 2:

```
5'-C-C-A-A-T-T-C-G-C-C-C-T-A-T-A-G-T-G-A-G-T-C-G-T-A-T-T----3'

3'-G-A-T-A-T-C-A-C-T-C-A-G-C-A-T-A-A-³²P-5'
```

Capping of the Primer with Thionucleotides

To the 18 µl annealing mixture add 10 µl of 100 µM $d_sGTP$, ddATP, ddTTP, and ddCTP and 4 µl (5 units) of diluted sequenase 2.0 (USB), and incubate the mixture for 2 min. at room temperature. According to the complementary strand this adds the following three nucleotides sequentially to the primer: $d_sG$, $d_sG$, ddC. The beads were sedimented using the magnet and the supernatant removed. The beads were then washed two times with 50 µl water.

Removing the Dideoxynucleotide from the Capped Primer

To the bead 10 µl (20 units) of an exonuclease solution 50 mM Tris/HCl pH 7.5, 5 mM MgCl2, 5 mM DTT were added and the mixture incubated 2 min. at 37° C. The reaction was stopped by sedimenting the beads with the magnet and removing the supernatant, followed by three washings with 50 µl of water. This step removed the dideoxy C-nucleotide from the 3'-end of the primer.

First Sequencing Cycle (9 Steps)

Scheme 1

Steps 2 and 3

The beads (anchored template/primer complex 2) were resuspended in 13 µl water. The following items were added: 5 µl 5× sequenase buffer, 10 µl of a nucleotide mixture containing 100 µM dCTP, 100 µM ddGTP, 100 µM ddATP, 100 µM ddTTP, and 4 µl of diluted sequenase 2.0. The mixture was incubated for 2 min. at 37° C. and the reaction stopped by sedimenting the beads with the magnet and removing the supernatant followed by three further washings with 50 µl of water. In this step, according to the complementary strand, one C-nucleotide and one dideoxy G-nucleotide were added to the 3-end of the capped primer.

Step 4

This step is omitted because the label is located on the primer.

Steps 5 and 6

The dideoxynucleotide and the labelled nucleotides were removed by adding 10 µl (20 units) of an exonuclease III solution 50 mM Tris/HCl pH 7.5 mM MgCl$_2$, 5 mM DTT and incubating the mixture for 2 min. at 37° C. The reaction was stopped by sedimenting the beads with the magnet and removing the supernatant, followed by three washings with 50 µl of water. The removal of the label was checked by measuring the mixture with the hand counter.

Steps 7 and 8

In order to cap the primer, the beads were resuspended in 13 µl water. The following items were added: 5 µl 5× sequenase buffer, 10 µl of a nucleotide mixture containing 10 µM $d_s$CTP, 100 µM ddGTP, 100 µM ddATP µM ddTTP, and 4 µl of diluted sequenase 2.0. The mixture was incubated 2 min. at 37° C. and the reaction stopped by sedimenting the beads with the magnet and removing the supernatant followed by three further washings with 50 µl of water. In this step, one thiolated C-nucleotide and one dideoxy G-nucleotide were added to the sequencing primer.

Steps 9 and 10

The dideoxy nucleotide was removed by adding 10 pi (20 units) of the above specified exonuclease III solution and incubating the mixture for 2 min. at 37° C. The reaction was stopped by sedimenting the beads with the magnet and removing the supernatant, followed by three washings with 50 µl of water.

Second Sequencing Cycle (9 Steps)

Scheme 1

Steps 2 and 3

The beads (anchored template/primer complex 2) were resuspended in 13 µl water. The following items were added: 5 µl 5× sequenase buffer, 10 µl of a nucleotide mixture containing 100 µM dGTP, 100 µM ddATP, 100 µM ddTTP, 100 µM ddCTP, and 4 µl of diluted sequenase 2.0. The mixture was incubated for 2 min. at 37° C. and the reaction stopped by sedimenting the beads with the magnet and removing the supernatant followed by three further washings with 50 µl of water. In this step, according to the complementary strand, one G-nucleotide and one dideoxy A-nucleotide were added to the 3'-end of the capped primer.

Step 4

This step is omitted because the label is located on the primer.

Steps 5 and 6

The dideoxynucleotide and the labelled nucleotides were removed by adding 10 µl (20 units) of an exonuclease III solution in 50 mM Tris/HCl pH 7.5, 5 mM MgCl$_2$, 5 mM DTT and incubating the mixture for 2 min. at 37° C. The reaction was stopped by sedimenting the beads with the magnet and removing the supernatant, followed by three washings with 50 µl of water. The removal of the label was checked by measuring the mixture with the hand counter.

Steps 7 and 8

In order to cap the primer, the beads were resuspended in 13 µl water. The following items were added: 5 µlx sequenase buffer, 10 µl of a nucleotide mixture containing 100 µM $d_s$GTP, 100 µM ddATP, 100 µM ddTTP, 100 µM ddCTP, and 4 µl of diluted sequenase 2.0. The mixture was incubated 2 min. at 37° C. and the reaction stopped by sedimenting the beads with the magnet and removing the supernatant followed by three further washings with 50 µl of water. In this steel, one thiolated G-nucleotide and one dideoxy A-nucleotide were added to the sequencing primer.

Steps 9 and 10

The dideoxy nucleotide was removed by adding 10 µl (20 units) of the above specified exonuclease III solution and incubating the mixture for 2 min at 37° C. The reaction was stopped by sedimenting the beads with the magnet and removing the supernatant, followed by three washings with 50 µl of water.

Third Sequencing Cycle (9 Steps)

Scheme 1

Steps 2 and 3

The beads (anchored template/primer complex 2) were resuspending in 13 µl water. The following items were added: 5 µl 5× sequenase buffer, 10 µl of a nucleotide mixture containing 100 µM dATP, 100 µM ddGTP, 100 µM ddTTP, 100 µM ddCTP, and 4 µl of diluted sequenase 2.0. The mixture was incubated for 2 min at 37° C. and the reaction stopped by sedimenting the beads with the magnet and removing the supernatant followed by three further washings with 50 µl of water. In this step, according to the complementary strand, two A-nucleotides and one dideoxy T-nucleotide were added at the 3'-end of the capped primer.

Step 4

This step is omitted because the label is located con the primer.

Steps 5 and 6

The dideoxynucleotide and the labelled nucleotides were removed by adding 10 µl (20 units) of an exonuclease III solution in 50 mM Tris/HCl pH 7.5, 5 mM MgCl$_2$, 5 mM DTT and incubating the mixture for 2 min. at 37° C. The reaction was stopped by sedimenting the beads with the magnet and removing the supernatant, followed by three washings with 50 µl of water. The removal of the label was checked by measuring the hand counter.

Steps 5 and 6

In order to cap the primer, the beads were resuspended in 13 µl water. The following items were added: 5 µl 5× sequenase buffer, 10 µl of nucleotide mixture containing 100 µM $d_s$ATP, 100 µM ddGTP, 100 µM ddTTP, 100 µM ddCTP, and 4 μl of diluted sequenase 2.0. The mixture was incubated 2 min. at 37° C. and the reaction stopped by sedimenting the beads with the magnet and removing the supernatant followed by three further washings with 50 μl of water. In this step, one thiolated A-nucleotide and one dideoxy T-nucleotide were added to the sequencing primer.

Steps 9 and 10

The dideoxy nucleotide was removed by adding 10 μl (20 units) of the above specified exonuclease III solution and incubating the mixture for 2 min at 37° C. The reaction was stopped by sedimenting the beads with the magnet and removing the supernatant, followed by three washings with 50 μl of water.

Fourth Sequencing Cycle (9 Steps)

Scheme 1

Steps 2 and 3

The beads (anchored template/primer complex 2) were resuspended in 13 μl water. The following items were added: 5 μl 5× sequenase buffer, 10 μl of a nucleotide mixture containing 10 μM dTTP, 100 μM ddGTP, 100 μM ddATP, 100 μM ddCTP, and 4 μl of diluted sequenase 2.0. The mixture was incubated for 2 min. at 37° C. and the reaction stopped by sedimenting the beads with the magnet and removing the supernatant followed by three further washings with 50 μl of water. In this step, according to the complementary strand, two T-nucleotides and one dideoxy G-nucleotide were added to the 3'-end of the capper primer.

Step 4

This step is omitted because the label located on the primer.

Steps 5 and 6

The dideoxynucleotide and the labelled nucleotides were removed by adding 10 μl (20 units) of an exonuclease III solution in 50 mM Tris/HCl pH 7.5, 5 mM MgCl$_2$, 5 mM DTT and incubating the mixture for 2 min. at 37° C. The reaction was stopped by sedimenting the beads with the magnet and removing the supernatant, followed by three washings with 50 μl of water. The removal of the label was checked by measuring the mixture with the hand counter.

Steps 7 and 8

In order to cap the primer, the beads were resuspended in 13 μl water. The following items were added: 5 μl 5× sequenase buffer, 10 μl of a nucleotide mixture containing 100 μM d$_s$TTP, 100 μM ddGTP, 100 μM ddATP, 100 μM ddCTP, and 4 μl of diluted sequenase 2.0. The mixture was incubated 2 min. at 37° C. and the reaction stopped by sedimenting the beads with the magnet and removing the supernatant followed by three further washings with 50 μl of water. In this step, one thiolated T-nucleotides and one dideoxy G-nucleotide were added to the sequencing primer.

Steps 9 and 10

The dideoxy nucleotide was removed by adding 10 μl (20 units) of the above specified exonuclease III solution and incubating the mixture for 2 min. at 37° C. The reaction was stopped by sedimenting the beads with the magnet and removing the supernatant, followed by three washings with 50 μl of water.

Example 5

Fluorescein was used as a single tag attached to all four deoxynucleotides. In particular we used the following fluorescein-labelled deoxynucleoside triphosphates: fluorescein-12-dUTP, fluorescein-15-dATP, fluorescein-15-dCTP, fluorescein-15-dITP.

Generation of Templates

As a model template we used two single-stranded PCR products which were derived from the multicloning site of Bluescript II KS. Amplification of the Bluescript II KS vector DNA using the biotinylated M13 (−21) forward primer and the nonbiotinylated M13 reverse primer yielded a PCR product which was anchored via the biotin moiety to streptavidin-coated beads as described in example 1. The nonbiotinylated (+) strand was removed by incubating the beads with 0.15M NaOH for 5 minutes followed by a wash with 0.15M NaOH and three washes with water.. The template, comprising the (−) strand of the multicloning site of the Bluescript II KS vector, was named PCR template 1. Amplification of the Bluescript II KS vector using the biotinylated M13 reverse primer and the nonbiotinylated Ml3 (−21) forward primer yielded a PCR product which was anchored via the biotin moiety to streptavidin-coated beads as described in example 1. The nonbiotinylated (−) strand was removed by incubating the beads with 0.15M NaOH for 5 minutes followed by a wash with 0.15M NaOH and three washes with water. This template comprising the (+) strand of the multicloning site of the Bluescript II KS vector was named PCR template 2.

Synthesis of 5'-TAMRA Labelled Specific Oligonucleotide Primers

For each fluorescently-labelled nucleotide four different primers were designed using the Bluescript sequence of the PCR template 1 and 2. The primers were located in front of runs of a single nucleotide allowing incorporation of one, two, three, four, or five nucleotides of the same kind.

| Name | Sequence | No. of incorporated fluorescent nucleotides | Nucleotide mix | template |
|---|---|---|---|---|
| For incorporation of fluorescein-12-dUTP the following primers were synthesized: | | | | |
| A | 5'-TAMRA-ACTATAGGGCGAATTGGAGC | 1 | dUTP-F,ddCTP | 1 |
| K | 5'-TAMRA-CGACTCACTATAGGGCGA | 2 | dATP,dUTP-F,ddGTP | 1 |
| G | 5'-TAMRA-GGTACCCAGCTTTTGTTCC | 3 | dCTP,dUTP-F,ddATP | 1 |
| L | 5'-TAMRA-GGGGGCCCGGTACCCAG | 4 | dCTP,dUTP-F,ddGTP | i |
| For incorporation of fluorescein-15-dCTP the following primers were synthesized: | | | | |
| G | 5'TAMRA-GGTACCCAGCTTTTGTTCC | 1 | dTTP,dCTP,F,ddATP, | 1 |
| A | 5'TAMRA-ACTATAGGGCGAATTGGAGC | 2 | dTTP,dCTP-F,ddATP | 1 |
| C | 5'TAMRA-TACGCCAAGCGCGCAATT | 3 | dATP,dCTP-F,ddTTP | 2 |
| D | 5'TAMRA-CGCTCTAGAACTAGTGGA | 5 | dTTP,dCTP,ddGTP | 1 |

| Name | Sequence | No. of incorporated fluorescent nucleotide | Nucleotide mix | template |
|---|---|---|---|---|
| | For incorporation of fluorescein-15-dATP the following primers were synthesized: | | | |
| G | 5'TAMRA-GGTACCCAGCTTTTGTTCC | 1 | dCTP,dTTP,dATP-F, ddGTP | 1 |
| T3 | 5'-TAMRA-ATTAACCCTCACTAAAG | 2 | dGTP,dATP-F,ddCTP | 2 |
| E | 5'-TAMRA-GCGCAATTAACCCTCACT | 3 | dATP-F,ddGTP | 2 |
| F | 5'-TAMRA-AACCCTCACTAAAGGGAA | 4 | dCTP,dATP-F,ddGTP | 1 |
| | For incorporation of fluorescein-15-dITP the followincg primers were synthesized: | | | |
| B | 5'-TAMRA-GCTATGACCATGATTAC | 1 | dITP-F,ddCTP | 2 |
| T3 | 5'-TAMRA-ATTAACCCTCACTAAAG | 2 | dITP-F,ddATP | 2 |
| M | 5'-TAMRA-CGCGTAATACGACTCACTAT | 3 | dATP,dITP-F,ddCTP | 1 |
| N | 5'-TAMRA-GATATCGAATTCCTGCAGCC | 4 | dCTP-dITP-F,ddATP | 1 |

Annealing

In sixteen different annealing reactions, 2 µl of water, 5 µl of the appropriate single-stranded PCR template 1 or 2 (see tables), 2 µl of 5× sequenase buffer and 1 µl (0.5 pmol) of the appropriate TAMRA-labelled primer (see tables) were combined, heated at 65° C. for 3 minutes and then incubated on ice.

Extension Reactions

In sixteen different extension reactions, to 6 µl of each annealing mix, ²ll of a nucleotide mixture (see tables) containing the appropriate unlabelled dNTPs (at 10 µM), the appropriate fluorescently-labelled dNTP (at 10 µM), and the appropriate ddNTP (at 10 µM), and 2 µl of diluted sequenase 2.0 were added and the mixture incubated at 37° C. for 3 minutes. The reactions were stopped by adding 5 µl of 80% formamide and heated for 3 min at 80° C. followed by sedimenting the beads with a magnet and removing the supernatant.

Detection/Imaging Step (Quantitation)

Figure 2:
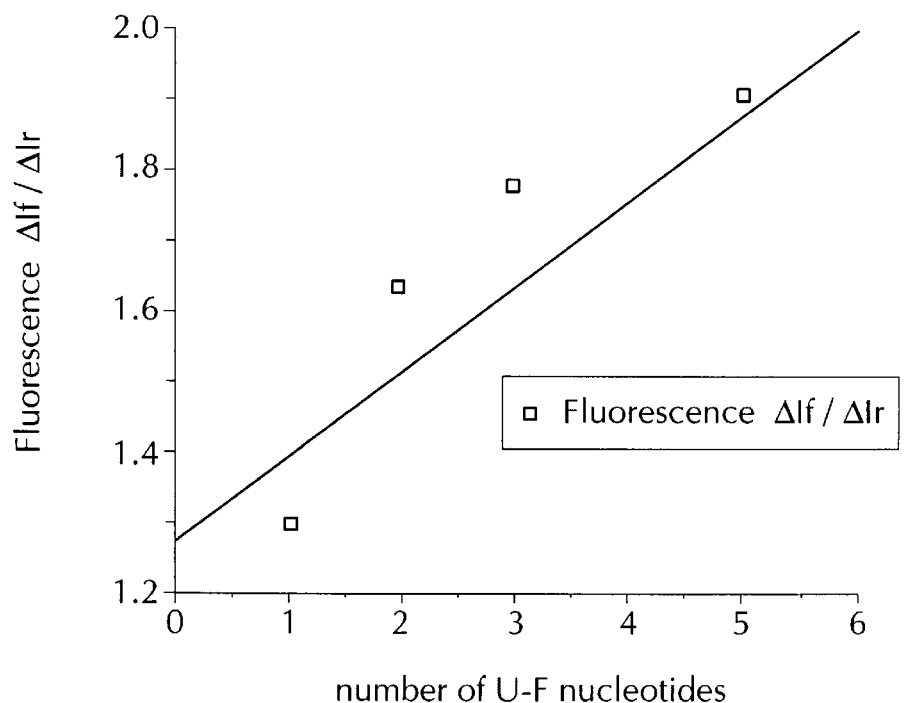

One µl of each supernatant was measured using a SIT camera (model C2 400-08, Hamamatsu Photonics SA) mounted on a fluorescence microscope. The emitted fluorescence of the rhodamine dye TAMRA located at the 5'-end of the primer and the fluorescein dye introduced by nucleotide incorporation at the 3'-end of the primer was determined for each sample using appropriate filter systems. A control sample of 80 formamide was also measured. The emitted fluorescence ΔI fluorescein and ΔI rhodamine was recorded. The ratio of ΔI fluorescein to ΔI rhodamine was used to normalise the data The results may be summarised as follows:

Incorporation of up to five fluorescein-labelled pyrimidine nucleotides (fluorescein-12-U, fluorescein-15-C):

Quantitative measurements show a linear correlation between emitted fluorescence and the number of incorporated fluorescein-labelled pyrimidine nucleotides. No quenching of fluorescence has been observed (see FIGS. 1 and 2).

Using the above mentioned detection/imaging system from Hamamatsu Photonics we were able to detect as little as; $10^8$ molecules in a volume of approx. 1 nl (concentration: 150 nM), allowing, in principle, the use of up to $10^4$ different templates on an array of 8 cm×8 cm.

Incorporation of up to two fluorescein-labelled purine nucleotides (fluorescein-15-A, fluorescein-15-I). Using the above detector system we were able to measure the difference between one and two fluorescein-labelled purine nucleotides.

Example 6

Preparation of the DNA Template/Primer Complex 1

Generation of template and binding to solid support, annealing of the sequencing primer to the anchored single-stranded DNA template, capping of the primer with thionucleotides, and removing of the dideoxynucleotide from the capped primer were carried out as in example 1.

Sequencing by Sequential Addition of Single Fluorescently-Labelled Nucleotides: First Complete Cycle of 9 Steps Scheme 1

Steps 2 and 3

The beads (anchored template/primer complex 1) were resuspended in 4 µl water. The following items were added: 2 µl 5× sequenase buffer, 2 µl of a nucleotide mix containing 10 µM fluorescein-15-dATP (Boehringer Mannheim), 10 µM ddGTP, 10 µM ddTTP, 10 µM ddCTP, and 2 µl of diluted sequenase 2.0. The mixture was incubated for 2 min at 37° C. and the reaction stopped by sedimenting the beads with the magnet and removing the supernatant followed by three further washings with 50 µl of water. In this step, according to the complementary strand, two fluorescein-15-A-nucleotides and one dideoxy T-nucleotide were added to the 3'-end of the capped primer.

Step 4

The fluorescence was measured using a SIT camera (model C2 400-08, Hamamatsu Photonics SA) mounted on a fluorescence microscope.

Steps 5 and 6

The dideoxynucleotide and the fluorescently-labelled nucleotides were removed by adding 10 µl (20 units) of an exonuclease-III solution in 50 µM Tris/HCl Ph 7.5, 5 mM MgCl₂, 5 mM DTT and incubating the mixture for 2 min at 37° C. The reaction was stopped by sedimenting the beads with the magnet and removing the supernatant, followed by three washings with 50 µl of water.

Steps 7 and 8

In order to cap the primer, the beads were resuspended in 4 µl water. The following items were added: 2 ll 5× sequenase buffer, 2 μl of a nucleotide mixture containing 10 μM d$_s$ATP, 10 μM ddGTP, 10 μM ddTTP, 10 μM ddCTP, and 2 μl of diluted sequenase 2.0. The mixture was incubated for 2 min at 37° C. and the reaction stopped by sedimenting the beads with the magnet and removing the supernatant followed by three further washings with 50 μl of water. In this step, two thiolated A-nucleotides and one dideoxy T-nucleotide were added to the sequencing primer.

Steps 9 and 10

The dideoxy nucleotide was removed by adding 10 μl (20 units) of the above specified exonuclease-III solution and incubating the mixture for 2 min at 37° C. The reaction was stopped by sedimenting the beads with the magnet and removing the supernatant, followed by three washing with 50 μl of water.

Sequencing by Sequential Addition of Single
Nucleotides: Second Complete Cycle of 9 Steps Scheme 1

Steps 2 and 3

The beads (anchored template/primer complex 1) were resuspended in 4 μl water. The following items were added: 2 μl of 5× sequenase buffer, 2 μl of a nucleotide mixture containing 10 μM fluorescein-12-dUTP (Boehringer Mannheim), 10 μM ddGTP, 10 μM ddATP, 10 μM ddCTP, and 2 μl of diluted sequenase 2.0. The mixture was incubated 2 min at 37° C. and the reaction stopped by sedimenting the beads with the magnet and removing the supernatant followed by three further washings with 50 μl of water. In this step, according to the complementary strand, two fluorescein-labelled U-nucleotides and one dideoxy G-nucleotide were added to the 3'-end of the capped primer.

Step 4

The fluorescence was measured using a SIT camera (model 400-08, Hamamatsu Photonics SA) mounted on a fluorescence microscope.

Steps 5 and 6

The dideoxynucleotide and the labelled nucleotides were removed by adding 10 μl (20 units) of the above specified exonuclease-III solution and incubating the mixture for 2 min at 37° C. The reaction was stopped by sedimenting the beads with the magnet and removing the supernatant, followed by three washings with 50 μl of water.

Steps 7 and 8

In order to cap the primer, the beads were resuspended in 4 μl water. The following items were added: 2 μl of 5× sequenase buffer, 2 μl of a nucleotide mixture containing 10 μM d$_s$TTP, 10 μM ddGTP, 10 μM ddATP, 10 μM ddCTP, and 2 μl of diluted sequenase 2.0. The mixture was incubated for 2 min at 37° C. and the reaction stopped by sedimenting the beads with the magnet and removing the supernatant followed by three further washings with 50 μl of water. In this step, two thiolated T-nucleotides and one dideoxy G-nucleotide were added to the sequencing primer.

Steps 9 and 10

The dideoxy nucleotide was removed by adding 10 μl (20 units) of the above specified exonuclease-III solution and incubating the mixture for 2 min at 37° C. The reaction was stopped by sedimenting the beads with the magnet and removing the supernatant, followed by three washings with 50 μl of water.

Example 7

Preparation of the DNA Template/Primer Complex

1

Generation of template and binding to solid support, annealing of the sequencing primer to the anchored single-stranded DNA template, capping of the primer with thionucleotides, and removing of the dideoxynucleotide from the capped primer were carried out as in example 1.

Sequencing by Sequential Addition of Single
Fluorescently-Labelled Nucleotides: First Complete
Cycle of 9 Steps Scheme 1

Steps 2 and 3

The beads (anchored template/primer complex 1) were resuspended in 4 μl water. The following items were added: 2 μl 5× sequenase buffer, 2 μl of a nucleotide mix containing 500 μM fluorescein-15-dATP, 1.0 μM dATP, 10 μM ddGTP, 10 μM ddTTP, 10 μM ddCTP, and 2 μl of diluted sequenase 2.0. The mixture was incubated for 2 min at 37° C. and the reaction stopped by sedimenting the beads with the magnet and removing the supernatant followed by three further washings with 50 μl of water. In this step, as directed by the complementary strand, fluorescein-15-A-nucleotides, A-nucleotides, and one dideoxy T-nucleotide were added to the 3'-end of the capped primer.

Step 4

The fluorescence was measured using a SIT camera (model C2 400-08, Hamamatsu Photonics SA) mounted on a fluorescence microscope.

Steps 5 and 6

The dideoxynucleotide, the deoxynucleotides and the fluorescently-labelled nucleotides were removed by adding 20 μl (20 units) of an exonuclease-III solution in 50 mM Tris/HCl pH 7.5, 5 mM MgCl$_2$ 5 μM DTT and incubating the mixture for 2 min at 37° C. The reaction was stopped by sedimending the beads with the magnet and removing the supernatant, followed by three washings with 50 μl of water.

Steps 7 and 8

In order to cap the primer, the beads were resuspended in 4 μl water. The following items were added: 2 μl 5× sequenase buffer, 2 μl of a nucleotide mixture containing 10 μM d$_s$ATP, 10 μM ddGTP, 10 μM ddTTP, 10 μM ddCTP, and 2 μl of diluted sequenase 2.0. The mixture was incubated for 2 min at 37° C. and the reaction stopped by sedimenting the beads with the magnet and removing the supernatant followed by the three further washings with 50 μl of water. In this step, two thiolated A-nucleotides and one dideoxy T-nucleotide were added to the sequencing primer.

Steps 9 and 10

The dideoxy nucleotide was removed by adding 10 μl (20 units) of the above specified exonuclease-III solution and incubating the mixture for 2 min at 37° C. The reaction was stopped by sedimenting the beads with the magnet and removing the supernatant, followed by three washings with 50 μl of water.

Sequencing by Sequential Addition of Single
Nucleotides: Second Complete Cycle of 9 Steps Scheme 1

Steps 2 and 3

The beads (anchored template/primer complex 1) were resuspended in 4 μl water. The following items were added: 2 μl of 5× sequenase buffer, 2 μl of a nucleotide mixture containing 15 μM fluorescein-12-dUTP, 1.0 μM dTTP, 10 μM ddGTP, 10 μM ddATP, 10 μM ddCTP, and 2 μl of diluted sequenase 2.0. The mixture was incubated for 2 min at 37° C. and the reaction stopped by sedimenting the beads with the magnet and removing the supernatant followed by three further washings with 50 μl of water. In this step, as directed by the complementary strand, fluorescein-labelled U-nucleotides, T-nucleotides, and one dideoxy G-nucleotide were added to the 3'-end of the capped primer.

Step 4
The fluorescence was measured using a SIT camera (model C2 400-08, Hamamatsu Photonics SA) mounted on a fluorescence microscope.

Steps 5 and 6
The dideoxynucleotide and the labelled nucleotides were removed by adding 10 µl (20 units) of the above specified exonuclease-III solution and incubating the mixture for 2 min at 37° C. The reaction was stopped by sedimenting the beads with the magnet and removing the supernatant, followed by three washings with 50 µl of water.

Steps 7 and 8
In order to cap the primer, the beads were resuspended in 4 µl water. The following items were added: 2 µl of 5× sequenase buffer, 2 µl of a nucleotide mixture containing 10 µM $d_s$TTP, 10 µM ddGTP, 10 µM ddATP, 10 µM ddCTP, and 2 µl of diluted sequenase 2.0. The mixture was incubated 2 min at 37° C. and the reaction stopped by sedimenting the beads with the magnet and removing the supernatant followed by three further washings with 50 µl of water. In this step, two thiolated T-nucleotides and one dideoxy G-nucleotide were added to the sequencing primer.

Steps 9 and 10
The dideoxy nucleotide was removed by adding 10 µl (20 units) of the above specified exonuclease-III solution and incubating the mixture for 2 min at 37° C. The reaction was stopped by sedimenting the beads with the magnet and removing the supernatant, followed by three washings with 50 µl of water.

Example 8

Preparation of the DNA Template/Primer Complex 1

Template preparation, binding of the template to a solid support, and annealing the sequencing primer was performed as described in example 1.

Capping of the Primer with Thionucleotides
To the 18 µl annealing mixture add 10 µl of 100 µM $d_s$GTP, ddATP, ddTTP, and ddCTP and 4 µl (5 units) of diluted sequenase 2.0 (USB), and incubate the mixture for 2 min at room temperature. As directed by the complementary strand, this adds the following three nucleotides sequentially to the primer: $d_s$G, $d_s$G, ddC. The beads were sedimented using the magnet and the supernatant removed. The beads were then washed two times with 50 µl water.

Removing the Dideoxynucleotide from the Capped Primer
To the beads, 10 µl (20 units) of an exonuclease solution in 50 mM Tris/HCl pH 7.5, 5 mM MgCl2, 5 mM DTT were added and the mixture incubated 2 min at 37° C. The reaction was the reaction stopped by sedimenting the beads with the magnet and removing the supernatant, followed by three washings with 50 µl of water. This step removed the dideoxy C-nucleotide from the 3'-end of the primer.

First Sequencing Cycle (9 Steps)
Scheme 1
Steps 2 and 3
The beads (anchored template/primer complex 1) were resuspended in 4 µl of water. The following items were added: 2 µl 5× sequenase buffer, 2 µl of a nucleotide mixture containing 10 µM fluorescein-15-dCTP (Boehringer Mannheim), 10 µM ddGTP, 10 µM ddATP, 10 µM ddTTP, and 2 µl of diluted sequenase 2.0. The mixture was incubated for 2 min at 37° C. and stopped by sedimenting the beads with the magnet and removing the supernatant followed by three further washings with 50 µl of water. In this step, as directed by the complementary strand, one fluorescein-labelled C-nucleotide and one dideoxy G-nucleotide were added to the 3'-end of the capped primer.

Step 4
The fluorescence was measured using a SIT camera (model C2 400-08, Hamamatsu Photonics SA) mounted on a fluorescence microscope.

Steps 5 and 6
The dideoxynucleotide and the fluorescein-labelled nucleotides were removed by adding 10 µl (20 units) of an exonuclease-III solution in 50 mM Tris/HCl pH 7.5, 5 mM MgCl$_2$, 5 mM DTT and incubating the mixture for 2 min at 37° C. The reaction was stopped by sedimenting the beads with the magnet and removing the supernatant, followed by three washings with 50 µl of water.

Steps 7 and 8
In order to cap the primer, the beads were resuspended in 4 µl water. The following items were added: 2 µl 5× sequenase buffer, 2 µl of a nucleotide mixture containing 10 µM $d_s$CTP, 10 µM ddGTP, 10 µM ddATP, 10 µM ddTTP, and 2 µl of diluted sequenase 2.0. The mixture was incubated 2 min at 37 ° C. and the reaction stopped by sedimenting the beads with the magnet and removing the supernatant followed by three further washings with 50 µl of water. In this step, one thiolated C-nucleotide and one dideoxy G-nucleotide were added to the sequencing primer.

Steps 9 and 10
The dideoxy nucleotide was removed by adding 10 l (20 units) of the above specified exonuclease-Ill solution and incubating the mixture for 2 min at 37° C. The reaction was stopped by sedimenting the beads with the magnet and removing the supernatant, followed by three washings with 50 µl of water.

Second Sequencing Cycle (9 Steps)
Scheme 1
Steps 2 and 3
The beads (anchored template/primer complex 1) were resuspended in 4 µl water. The following items were added: 2 µl 5× sequenase buffer, 2 µl of a nucleotide mixture containing 10 µM fluorescein-15-dITP (Boehringer Mannheim), 10 µM ddATP, 10 µM ddTTP, 10 µM ddCTP, and 2 µl of diluted sequenase 2.0. The mixture was incubated 2 min at 37° C. and the reaction stopped by sedimenting the beads with the magnet and removing the supernatant followed by three further washings with 50 µl of water. In this step, as directed by the complementary strand, one fluorescein-labelled I-nucleotide and one dideoxy A-nucleotide were added to the 3'-end of the capped primer.

Step 4
The fluorescence was measured using a SIT camera (model C2 400-08, Hamamatsu Photonics SA) mounted on a fluorescence microscope.

Steps 5 and 6
The dideoxynucleotide and the labelled nucleotide were removed by adding 10 µl (20 units) of an exonucleaseIII solution in 50 mM Tris/HCl pH 7.5, 5 mM MgCl$_2$, 5 mM DTT and incubating the mixture for 2 min at 37° C. The reaction was stopped by sedimenting the beads with the magnet and removing the supernatant, followed by three washings with 50 µl of water.

Steps 7 and 8
In order to cap the primer, the beads were resuspended in 4 µl water. The following items were added: 2 µl 5× sequenase buffer, 2 µl of a nucleotide mixture containing 10 µM $d_s$GTP, 10 µM ddATP, 10 µM ddTTP, 10 µM ddCTP, and 2 µl of diluted sequenase 2.0. The mixture was incubated for 2 min at 37° C. and the reaction stopped by sedimenting the beads with the magnet and removing the supernatant followed by three further washings with 50 µl of water. In this step, one thiolated G-nucleotide and one dideoxy A-nucleotide were added to the sequencing primer.

Steps 9 and 10

The dideoxy nucleotide was removed by adding 10 µl (20 units) of the above specified exonuclease III solution and incubating the mixture for 2 min at 37° C. The reaction was stopped by sedimenting the beads with the magnet and removing the supernatant, followed by three washings with 50 µl of water.

Third Sequencing Cycle (9 Steps)

Scheme 1

Steps 2 and 3

The beads (anchored template/primer complex 1) were resuspended in 4 µl water. The following items were added: 2 µl 5× sequenase buffer, 2 µl of a nucleotide mixture containing 10 µM fluorescein-15-dATP, 10 µM ddGTP, 10 µM ddTTP, 10 µM ddCTP, and 2 µl of diluted sequenase 2.0. The mixture was incubated for 2 min at 37° C. and the reaction stopped by sedimenting the beads with a magnet and removing the supernatant followed by three further washings with 50 µl of water. In this step, as directed by the complementary strand, two fluorescein-labelled A-nucleotides and one dideoxy T-nucleotide were added to the 3'-end of the capped primer.

Step 4

The fluorescence was measured using a SIT camera (model C2 400-08, Hamamatsu Photonics SA) mounted on a fluorescence microscope.

Steps 5 and 6

The dideoxynucleotide and the labelled nucleotides were removed by adding 10 µl (20 units) of an exonuclease-III solution in 50 mM Tris/HCl pH 7.5, 5 mM MgCl$_2$, 5 mM DTT and incubating the mixture for 2 min at 37° C. The reaction was stopped by sedimenting the beads with the magnet and removing the supernatant, followed by three washings with 50 µl of water.

Steps 7 and 8

In order to cap the primer, the beads were resuspended in 4 µl water. The following items were added: 2 µL 5× sequenase buffer, 2 µl of a nucleotide mixture containing 10 µM d$_s$ATP, 10 µM ddGTP, 10 µM ddTTP, 10 µM ddCTP, and 2 µl of diluted sequenase 2.0. The mixture was incubated 2 main at 37° C. and the reaction stopped by sedimenting the beads with the magnet and removing the supernatant followed by three further washings with 50 µl of water. In this step, two thiolated A-nucleotides and dideoxy T-nucleotide were added to the sequencing primer.

Steps 9 and 10

The dideoxy nucleotide was removed by adding 10 µl (20 units) of the above specified exonuclease III solution and incubating the mixture for 2 min at 37° C. The reaction was stopped by sedimenting the beads with the magnet and removing the supernatant, followed by three washings with 50 µl of water.

Fourth Sequencing Cycle (9 Steps)

Scheme 1

Steps 2 and 3

The beads (anchored template/primer complex 1) were resuspended in 4 µl water. The following items were added: 2 µl 5× sequenase buffer, 2 µl of a nucleotide mixture containing 10 µM fluorescein-12-dUTP, 10 µM ddGTP, 10 µM ddATP, 10 µM ddCTP, and 2 µl of diluted sequenase 2.0. The mixture was incubated for 2 min at 37° C. and the reaction stopped by sedimenting the beads with the magnet and removing the supernatant followed by three further washings with 50 µl of water. In this step, as directed by the complementary strand, two fluorescein-labelled U-nucleotides and one dideoxy G-nucleotide were added to the 3'-end of the capped primer.

Step 4

The fluorescence was measured using a SIT camera (model C2 400-08, Hamamatsu Photonics SA) mounted on a fluorescence microscope.

Steps 5 and 6

The dideoxynucleotide and the labelled nucleotides were removed by adding 10 µl (20 units) of an exonuclease-III solution in 50 mM Tris/HCl pH 7.5, 5 mM MgCl$_2$, 5 mM DTT and incubating the mixture for 2 min at 37° C. The reaction was stopped by sedimenting the beads with the magnet and removing the supernatant, followed by three washings with 50 µl of water. The removal of the label was checked by measuring the mixture with the hand counter.

Steps 7 and 8

In order to cap the primer, the beads were resuspended in 4 µl water. The following items were added: 2 µl 5× sequenase buffer, 2 µl of a nucleotide mixture containing 10 µM d$_s$TTP, 10 µM ddGTP, 10 µM ddATP, 10 µM ddCTP, and 2 µl of diluted sequenase 2.0. The mixture was incubated for 2 min at 37° C. and the reaction stopped by sedimenting the beads with the magnet and removing the supernatant followed by three further washings with 50 µl of water. In this step, two thiolated T-nucleotides and one dideoxy G-nucleotide were added to the sequencing primer.

Steps 8 and 9

The dideoxy nucleotide was removed by adding 10 µl (20 units) of the above specified exonuclease-III solution and incubating the mixture for 2 min at 37° C. The reaction was stopped by sedimenting the beads with the magnet and removing the supernatant, followed by three washings with 50 µl of water.

Example 9

Preparation of the DNA Template/Primer Complex 1

Template preparation, binding of the template to solid support, and annealing of the sequencing primer was performed as described in example 1.

Capping of the Primer with Thionucleotides

To the 18 µl annealing mixture add 10 µl of 100 µM d$_s$GTP, ddATP, ddTTP, and ddCTP and 4 µl (5 units) of diluted sequenase 2.0 (USB), and incubate the mixture for 2 min at room temperature. As directed by the complementary strand this adds the following three nucleotides sequentially to the primer: d$_s$G, d$_s$G, ddC. The beads were sedimented using the magnet and the supernatant removed. The beads were then washed two times with 50 µl water.

Removing the Dideoxynucleotide from the Capped Primer

To the beads, 10 µl (20 units) of an exonuclease solution in 50 mM Tris/HCl pH 7.5, 5 mM MgCl$_2$, 5 mM DTT were added and the mixture incubated 2 min at 37° C. The reaction was stopped by sedimenting the beads with the magnet and removing the supernatant, followed by three washings with 50 µl of water. This step removed the dideoxy C-nucleotide from the 3'-end of the primer.

First Sequencing Cycle (9 Steps)

Scheme 1

Steps 2 and 3

The beads (anchored template/primer complex 1) were resuspended in 4 µl water. The following items were added:

2 μl 5× sequenase buffer, 2 μl of a nucleotide mixture containing 15 μM fluorescein-15-dCTP, 1.0 μM dCTP, 10 μM ddGTP, 10 μM ddATP, 10 μM ddTTP, and 2 μl of diluted sequenase 2.0. The mixture was incubated for 2 min at 37° C. and the reaction stopped by sedimenting the beads with the magnet and removing the supernatant followed by three further washings with 50 μl of water.

Step 4

The fluorescence was measured using a SIT camera (model C2 400-08, Hamamatsu Photonics SA) mounted on a fluorescence microscope.

Steps 5 and 6

The dideoxynucleotide and the fluorescein-labelled nucleotides were removed by adding 10 μl (20 units) of an exonuclease-III solution in 50 mM Tris/HCl pH 7.5, 5 mM $MgCl_2$, 5 mM DTT and incubating the mixture for 2 min at 37° C. The reaction was stopped by sedimenting the beads with the magnet and removing the supernatant, followed by three washings with 50 μl of water.

Steps 7 and 8

In order to cap the primer, the beads were resuspended in 4 μl water. The following items were added: 2 μl 5× sequenase buffer, 2 μl of a nucleotide mixture containing 10 μM $d_s$CTP, 10 μM ddGTP, 10 μM ddATP, 10 μM ddTTP, and 2 μl of diluted sequenase 2.0. The mixture was incubated 2 min at 37° C. and the reaction stopped by sedimenting the beads with the magnet and removing the supernatant followed by three further washings with 50 μl of water. In this step, two thiolated C-nucleotides and one dideoxy G-nucleotide were added to the sequencing primer.

Steps 9 and 10

The dideoxy nucleotide was removed by adding 10 μl (20 units) of the above specified exonuclease III solution and incubating the mixture for 2 min at 37° C. The reaction was stopped by sedimenting the beads with the magnet and removing the supernatant, followed by three washings with 50 μl of water.

Second Sequencing Cycle (9 Steps)

Scheme 1

Steps 2 and 3

The beads (anchored template/primer complex 1) were resuspended in 4 μl water. The following items were added: 2 μl 5× sequenase buffer, 2 μl of a nucleotide mixture containing 500 μM fluorescein-15-dITP, 1.0 μM dGTP, 10 μM ddATP, 10 μM ddTTP, 10 μM ddCTP, and 2 μl of diluted sequenase 2.0. The mixture was incubated for 2 min at 37° C. and the reaction stopped by sedimenting the beads with the magnet and removing the supernatant followed by three further washings with 50 μl of water.

Step 4

The fluorescence was measured using a SIT camera (model c2 400-08, Hamamatsu Photonics SA) mounted on a fluorescence microscope.

Steps 5 and 6

The dideoxynucleotide and the labelled nucleotides were removed by adding 10 μl (20 units) of an exonuclease-III solution in 50 mM Tris/HCl pH 7.5, 5 mM $MgCl_2$, 5 mM DTT and incubating the mixture for 2 min at 37° C. The reaction was stopped by sedimenting the beads with the magnet and removing the supernatant, followed by three washings, with 50 μl of water.

Steps 7 and 8

In order to cap the primer, the beads were resuspended in 4 μl water. The following items were added: 2 μl 5× sequenase buffer, 2 μl of a nucleotide mixture containing 10 μM $d_s$GTP, 10 μM ddATP, 10 μM ddTTP, 10 μM ddCTP, and 2 μL of diluted sequenase 2.0. The mixture was incubated 2 min at 37° C. and the reaction stopped by sedimenting the beads with the magnet and removing the supernatant followed by three further washings with 50 μl of water. In this step, one thiolated G-nucleotide and one dideoxy A-nucleotide were added to the sequencing primer.

Step 9 and 10

The dideoxy nucleotide was removed by adding 10 μl (20 units) of a specified exonuclease-III solution and incubating the mixture for 2 min at 37° C. The reaction was stopped by sedimenting the beads with the magnet and removing the supernatant, followed by three washings with 50 μl of water.

Third Sequencing Cycle (9 Steps)

Scheme 1

Steps 2 and 3

The beads (anchored template/primer complex 1) were resuspended in 4 μl water. The following items were added: 2 μl 5× sequenase buffer, 2 μl of a nucleotide mixture containing 500 μM fluorescein-15-dATP, 1 μM dATP, 10 μM ddGTP, 10 μM ddTTP, 10 μM ddCTP, and 2 μl of diluted sequenase 2.0. The mixture was incubated for 2 min at. 37° C. and the reaction stopped by sedimenting the beads with the magnet and removing the supernatant followed by three further washings with 50 μl of water.

Step 4

The fluorescence was measured using a SIT camera (model C2 400-08, Hamamatsu Photonics SA) mounted on a fluorescence microscope.

Steps 5 and 6

The dideoxynucleotide and the labelled nucleotides were removed by adding 10 μl (20 units) of an exonuclease-III solution in 50 mM Tris/HCl pH 7.5, 5 mM $MgCl_2$, 5 mM DTT and incubating the mixture for 2 min at 37° C. The reaction was stopped by sedimenting the beads with the magnet and removing the supernatant, followed by three washings with 50 μl of water.

Steps 7 and 8

In order to cap the primer, the beads were resuspended in 4 μl water. The following items were added: 2 μl 5× sequenase buffer, 2 μl of a nucleotide mixture containing 10 μM $d_s$ATP, 10 μM ddGTP, 10 μM ddTTP, 10 μM ddCTP, and. 2 μl of diluted sequenase 2.0. The mixture was incubated 2 min at 37° C. and the reaction stopped by sedimenting the beads with the magnet and removing the supernatant followed by three further washings with 50 μl of water. In this step, two thiolated A-nucleotides and one dideoxy T-nucleotide were added to the sequencing primer.

Steps 9 and 10

The dideoxy nucleotide was removed by adding 10 pi (20 units) of the above specified exonuclease-III solution and incubating the mixture for 2 min at 37° C. The reaction was stopped by sedimenting the beads with the magnet and removing the supernatant, followed by three washings with 50 μl of water.

Fourth Sequencing Cycle (9 Steps)

Scheme 1

Steps 2 and 3

The beads (anchored template/primer complex 1) were resuspended in 4 μl water. The following items were added: 2 μl 5× sequenase buffer, 2 μl of a nucleotide mixture containing 15 μM fluorescein-12-dUTP, 1.0 μM dTTP, 10 μM ddGTP, 10 μM ddATP, 10 μM ddCTP, and 2 μl of diluted sequenase 2.0. The mixture was incubated for 2 min at 37° C. and the reaction stopped by sedimenting the beads with the magnet and removing the supernatant followed by three further washings with 50 μl of water.

Step 4

The fluorescence was measured using a SIT camera (model C2 400-08, Hamamatsu Photonics SA) mounted on a fluorescence microscope.

Steps 5 and 6

The dideoxynucleotide and the labelled nucleotides were removed by adding 10 μl (20 units) of an exonuclease-III solution in 50 mM Tris/HCl pH 7.5, 5 mM MgCl$_2$, 5 mM DTT and incubating the mixture for 2 min at 37° C. The reaction was stopped by sedimenting the beads with the magnet and removing the supernatant, followed by three washings with 50 μl of water. The removal of the label was checked by measuring the mixture with the hand counter.

Steps 7 and 8

In order to cap the primer, the beads were resuspended in 4 μl water. The following items were added: 2 μl 5× sequenase buffer, 2 μl of a nucleotide mixture containing 10 μM d$_s$TTP, 10 μM ddGTP, 10 μM ddATP, 10 μM ddCTP, and 2 μl of diluted sequenase 2.0. The mixture was incubated 2 min at 37° C. and the reaction stopped by sedimenting the beads with the magnet and removing the supernatant followed by three further washings with 50 μl of water. In this step, two thiolated T-nucleotides and one dideoxy G-nucleotide were added to the sequencing primer.

Steps 8 and 9

The dideoxy nucleotide was removed by adding 10 μl (20 units) of the above specified exonucleaseIII solution and incubating the mixture for 2 min at 37° C. The reaction was stopped by sedimenting the beads with the magnet and removing the supernatant, followed by three washings with 50 μl of water.

It will be understood that the invention is described above by way of example only, and that a variety of modifications will be apparent to those skilled in the art which fall within the scope of the appended claims.

What is claimed is:

1. A method for determining the sequence of a nucleic acid comprising the steps of:
   (a) forming a single-stranded template comprising the nucleic acid to be sequenced;
   (b) hybridizing a primer to the template to form a template/primer complex;
   (c) extending the primer by the addition of a single labelled nucleotide which is not a chain elongation inhibitor;
   (d) determining the type of the labelled nucleotide added onto the primer;
   (e) removing or neutralizing the label; and
   (f) repeating steps (c) to (e) sequentially and recording the order of incorporation of labelled nucleotides.

2. The method according to claim 1 wherein the template/primer complex of said step (b) is bound to a solid-phase support.

3. The method according to claim 1 wherein said extending step (c) further comprises the addition of unlabelled nucleotides.

4. The method according to claim 1 wherein said extending step (c) is carried out in the presence of a non-labelled chain elongation inhibitor.

5. The method according to claim 4, wherein said non-labelled chain elongation inhibitor is incorporated into the template/primer complex, and step (e) further comprises removing said non-labelled chain elongation inhibitor.

6. The method according to claim 4 wherein said non-labelled chain elongation inhibitor is not incorporated into said template/primer complex.

7. The method according to claim 6 wherein said non-labelled chain elongation inhibitor is selected from the group consisting of deoxynucleoside 5'-[α,β-methylene] triphosphates, deoxynucleoside diphosphates, and deoxynucleoside monophosphates.

8. The method according to claim 1 wherein said template/primer complex comprises a primer linked through its 3' terminus to a deoxynucleoside phosphorothioate base.

9. The method according to claim 8 wherein step (e) comprises:
   i) removing the labelled nucleotide with an exonuclease; and
   ii) replacing the labelled nucleotide with a corresponding unlabelled phosphorothioate nucleoside derivative in the presence of a non-labelled chain elongation inhibitor.

10. The method according to claim 1 wherein said steps (c) and (d) are repeated sequentially a multiplicity of times before said step (e).

11. The method according to claim 1 wherein the label is a fluorescent label and said step (e) comprises a process selected from the group consisting of neutralizing the label by bleaching with laser radiation, neutralizing the label using a chemical, and dissociating the label from the labelled nucleotide.

12. A process for sequencing a DNA fragment comprising the steps of:
   i) hybridizing a capped primer comprising a phosphorothioate nucleoside derivative to a template to form a template/primer complex;
   ii) adding a labelled deoxynucleoside triphosphate together with a mixture of non-labelled heterogenous chain terminators and a polymerase to the template/primer complex, wherein said labelled deoxynucleoside triphosphate is not a chain elongation inhibitor;
   iii) removing excess reagents by washing;
   iv) treating the template/primer complex with an exonuclease to remove both the labelled nucleotide resulting from incorporation of said labelled deoxynucleoside, and the non-labelled chain terminators;
   vi) removing the exonuclease by washing;
   vii) adding a phosphorothioate deoxynucleoside triphosphate corresponding to the labelled deoxynucleoside triphosphate added in step (ii) together with a mixture of non-labelled heterogeneous chain terminators;
   viii) removing excess reagents by washing;
   ix) treating the template/primer complex with an exonuclease to remove the non-labelled chain terminators; and
   x) removing the exonuclease by washing.

13. A process for sequencing a DNA fragment comprising the steps of:
   i) hybridizing a capped primer containing a phosphorothioate nucleoside derivative to a template to form a template/primer complex;
   ii) adding a labelled deoxynucleotide together with non-labelled heterogeneous chain terminators and a suitable polymerase, wherein said labelled deoxynucleotide is not a chain elongation inhibitor;
   iii) removing excess reagents by washing;
   iv) measuring the a mount of incorporated label;
   v) removing the labelled nucleotide and the terminators with an exonuclease;
   vi) removing the exonuclease by washing;

vii) adding a phosphorothioate deoxynucleotide together with a mixture of non-labelled heterogeneous chain elongation inhibitors not incorporated into the chain; and viii) removing excess reagents by washing.

14. A process for sequencing a DNA fragment comprising the steps of:
   i) hybridizing a capped primer containing a phosphorothioate deoxynucleotide to a template to form a template/primer complex;
   ii) adding a labelled nucleotide triphosphate together with a mixture of non-labelled heterogenous chain elongation inhibitors not incorporated into the chain, wherein said labelled nucleotide triphosphate is not a chain elongation inhibitor;
   iii) removing excess reagents by washing;
   iv) measuring the amount of incorporated label;
   v) repeating said steps ii, iii and iv sequentially until all four different labelled nucleotides in the presence of their corresponding, non-labelled heterogeneous chain elongation inhibitors not incorporated into the chain have been added;
   vi) removing all labelled nucleotides with exonuclease;
   vii) removing the exonuclease by washing;
   viii) adding the phosphorothioate deoxynucleotide corresponding to the first labelled deoxynucleotide added to the reaction in said step ii, together with non-labelled heterogenous chain elongation inhibitors not incorporated into the chain and a polymerase;
   ix) removing excess reagents by washing; and
   x) repeating said steps viii and ix with the three remaining phosphorothioate deoxynucleoside derivatives.

15. A process for sequencing a DNA fragment comprising the steps of:
   i) hybridizing a capped primer to a template to form a template/primer complex;
   ii) adding a fluorescent nucleoside triphosphate, together with three non-labelled heterogeneous chain elongation inhibitors not incorporated into the chain and a polymerase, wherein said fluorescent nucleoside triphosphate is not a chain elongation inhibitor;
   iii) removing excess reagents by washing;
   iv) measuring the amount of incorporated label;
   v) repeating said steps ii, iii, and iv using all three different nucleoside triphosphates, each with a fluorescent label, in the presence of the respective non-labelled heterogeneous chain elongation inhibitors not incorporated into the chain; and
   vi) destroying the fluorescent labels by bleaching with a laser of by a suitable chemical reaction, or removing the fluorescent labels by a chemical cleavage step.

16. A DNA sequencing kit comprising:
   i) a linker for attaching a DNA template to a solid-phase matrix the liner comprising a primer having a phosphorothioate deoxynucleoside residue at its 3' end;
   ii) non-labelled chain elongation inhibitors;
   iii) labelled nucleoside triphosphates which are not chain elongation inhibitors;
   iv) phosphorothioate deoxynucleoside triphosphates;
   v) a 5'→3' DNA polymerase; and
   vi) a 3'→5' exonuclease.

* * * * *

UNITED STATES PATENT AND TRADEMARK OFFICE
CERTIFICATE OF CORRECTION

PATENT NO. : 6,087,095
DATED : July 11, 2000
INVENTOR(S) : Rosenthal et al.

It is certified that error appears in the above-identified patent and that said Letters Patent is hereby corrected as shown below:

Column 1,
Line 40, change "achievers" to -- achieved --.

Column 12,
Line 65, change "5" to -- 50 --.

Column 17,
Line 53, change "pi" to -- µl --.

Column 21,
Line 30, change "211" to -- 2 µl --.
Line 49, change "80" to -- 80% --.

Column 26,
Line 28, change "1" to -- µl --.

Column 34, claim 16,
Line 24, change "liner" to -- linker --.

Signed and Sealed this

Eighteenth Day of September, 2001

Attest:

*Nicholas P. Godici*

NICHOLAS P. GODICI
*Attesting Officer* *Acting Director of the United States Patent and Trademark Office*